United States Patent [19]
Vlattas

[11] Patent Number: 5,371,096
[45] Date of Patent: Dec. 6, 1994

[54] (3-PYRIDYL)TETRAFURAN-2-YL SUBSTITUTED CARBOXYLIC ACIDS

[75] Inventor: Isodoros Vlattas, Summit, N.J.

[73] Assignee: Ciba-Geigy Corporation, Ardsley, Pa.

[21] Appl. No.: 113,551

[22] Filed: Aug. 27, 1993

[51] Int. Cl.$^5$ ............... C07D 405/04; A61K 31/435
[52] U.S. Cl. ..................... 514/336; 546/283
[58] Field of Search .................. 546/283; 514/336

[56] References Cited

U.S. PATENT DOCUMENTS

| | | | |
|---|---|---|---|
| 3,881,017 | 4/1975 | Vlattas | 514/445 |
| 3,883,659 | 5/1975 | Vlattas | 514/473 |
| 4,041,047 | 8/1977 | Vlattas | 549/66 |
| 4,077,979 | 3/1978 | Vlattas | 549/66 |
| 4,088,877 | 5/1978 | Vlattas | 514/473 |
| 4,482,549 | 11/1984 | Collington et al. | 514/183 |
| 4,542,151 | 9/1985 | Das | 514/438 |
| 5,053,415 | 10/1991 | Brewster et al. | 514/336 |

OTHER PUBLICATIONS

Derwent Abstract 88:366149/51, 1988 Corresponding to JP 63,277,655.
DeMais et al., Thromboxane A$_2$ Receptor Antagonists, Synthesis and Activities of Phenylsufonamido Derivatives, Eur. J. Med. Chem. 26, pp. 821–827 (1991).
Kawada et al., Synthesis of Monocyclic Analogues of a Potent Thromboxane Receptor Antagonist, (±)-(5-2)-7-[3-Endo-[(Phenylsulfonyl)Amino]Bicyclo [2.2.1]Hept-2-Exo-Yl]Heptenoic Acid (S-145), Heterocycles, 28, pp. 573–578 (1989).
Chem. Abstr. 104:148585 (1985) For A,E Below.
Thiem et al., Synthese von Oxaprostaglandinen Aus 1,4:3,6-Dianhydro-D-Sorbit, Liebigs Ann. Chem., pp. 2151–2164 (1985).
Maconochie et al., Evaluation of the Vascular Thromboxane A$_2$ Receptor Blocking Activity of GR32191 in Man, Proceedings of the BPS, p. 662P, Jul. 6–8, 1988.

*Primary Examiner*—Jane T. Fan
*Attorney, Agent, or Firm*—Barbara J. Ikeler; Nobert Gruenfeld

[57] ABSTRACT

Disclosed are compounds of formula

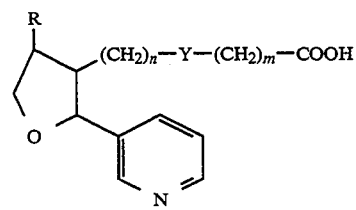

(I)

wherein R is OR' and R' is aryl-lower alkyl, biaryl-lower alkyl, lower alkyl or cycloalkyl-lower alkyl; or R is arylsulfonylamido;

n is 1, 2 or 3;
m is 1, 2 or 3;
Y is vinylene, ethylene or methyleneoxy; a stereoisomer or optical isomer thereof; and their pharmaceutically acceptable esters or salts; which are useful as thromboxane synthetase inhibitors and thromboxane receptor antagonists.

12 Claims, No Drawings

(3-PYRIDYL)TETRAFURAN-2-YL SUBSTITUTED CARBOXYLIC ACIDS

SUMMARY OF THE INVENTION

The present invention is concerned with certain (2-(3-pyridyl)tetrahydrofuran-3-yl)$C_{5-9}$alkanoic acids, (2-(3-pyridyl)tetrahydrofuran-3-yl)$C_{5-9}$alkenoic acids and (2-(3-pyridyl)tetrahydrofuran-3-yl)$C_{1-4}$alkylenoxy-$C_{2-5}$alkanoic acids and derivatives thereof which are useful as inhibitors of thromboxane synthetase, as well as thromboxane $A_2$ and prostaglandin $H_2$ receptor antagonists in mammals. The compounds of the invention are thus e.g. especially useful in suppressing the biological effects of endogenous thromboxane $A_2$, e.g. so as to inhibit vasoconstriction and platelet aggregation, in mammals.

The compounds of the invention by virtue of their inhibition of the enzyme thromboxane synthetase modulate the arachidonic acid cascade. They not only reduce the level of endogenous thromboxane $A_2$ synthesized and available to act as agonist at the thromboxane $A_2$ receptor, but can also cause an increase of the level of endogenous prostacyclin; such is beneficial, e.g. in certain cardiovascular conditions, by inhibiting platelet aggregation and also causing vasodilation. Furthermore, the thromboxane $A_2$ receptor blocking activity of the compounds of the invention inhibits the still available endogenous thromboxane $A_2$, as well as prostaglandin $H_2$, from exerting their biological effects, e.g. in causing platelet aggregation and vasoconstriction.

The compounds of the invention are thus particularly useful when administered alone or in combination to mammals for the treatment or prevention of conditions or syndromes in which the effect of endogenous thromboxane is implicated. Such comprise particularly cardiovascular disorders, primarily occlusive vascular conditions involving platelet aggregation such as peripheral vascular diseases, thrombosis, atherosclerosis, cerebral infarctions (strokes) and primary myocardial infarctions (heart attacks), as well as angina (stable and unstable) and hypertension, such as pregnancy induced hypertension. The compounds of the invention can also be used for prevention of reocclusion associated with angioplasty and coronary bypass surgery, and as adjuncts to prevent post-thrombolytic reocclusion from occurring after treatment with thrombolytic agents such as alteplase (also named TPA or tissue plasminogen activator), urokinase, streptokinase, anisoylated plasminogen streptokinase activator complex (APSAC, anistreplase), and related compounds, and to potentiate the thrombolytic effect of said thrombolytic agents. The compounds of the invention can further be used in the treatment of pulmonary disorders, such as bronchial asthma; in conjunction with transplants and immunosuppressive therapy, e.g. with cyclosporine to minimize cyclosporine-induced nephrotoxicity; to improve kidney function, e.g. in lupus nephritis and diabetic nephropathy; to prevent or reduce platelet loss during extracorporeal circulation; in conjunction with other cardiovascular agents, e.g. angiotensin-converting enzyme inhibitors, serotonin-2 inhibitors, calcium channel blockers, beta-blockers and anticoagulants (such as hirudin, desulfatohirudin and heparin) to enhance their cardiovascular effects; and to minimize side effects (e.g. anaphylactoid reaction) induced by protamine, e.g. when protamine is used for reversal of anticoagulant effect of heparin.

DETAILED DESCRIPTION OF THE INVENTION

More particularly the instant invention is concerned with compounds of formula I

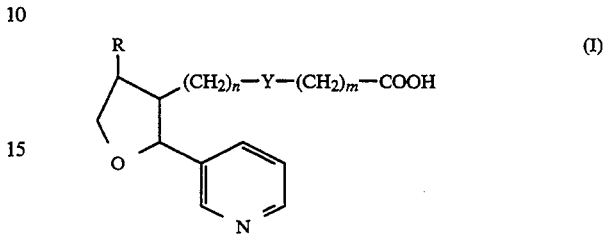

wherein R is OR' and R' is aryl-lower alkyl, biaryl-lower alkyl, lower alkyl or cycloalkyl-lower alkyl; or R is arylsulfonylamido; n is 1, 2 or 3; m is 1, 2 or 3; Y is vinylene, ethylene or methyleneoxy; or a stereoisomer or optical isomer thereof; or a pharmaceutically acceptable ester thereof; or a pharmaceutically acceptable salt thereof;

A particular embodiment of the invention is concerned with compounds of formula II

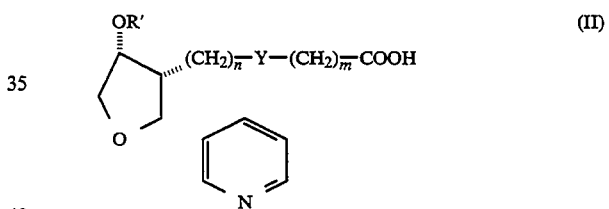

wherein R' is aryl-lower alkyl, biaryl-lower alkyl, lower alkyl or cycloalkyl-lower alkyl; n is 1, 2 or 3; m is 1, 2 or 3; Y is vinylene, ethylene or methyleneoxy; or a pharmaceutically acceptable ester thereof; or a pharmaceutically acceptable salt thereof.

A further preferred embodiment of the invention relates to the compounds of formula III

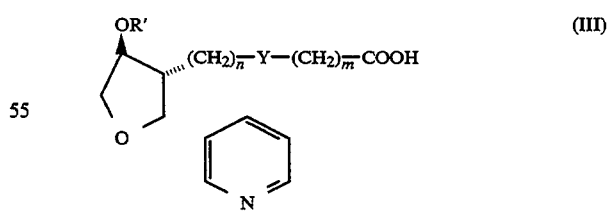

wherein R' is aryl-lower alkyl, biaryl-lower alkyl, lower alkyl or cycloalkyl-lower alkyl; n is 1, 2 or 3; m is 1, 2 or 3; Y is vinylene, ethylene or methyleneoxy; or a pharmaceutically acceptable ester thereof; or a pharmaceutically acceptable salt thereof.

A further preferred embodiment of the invention relates to the compounds of formula IV

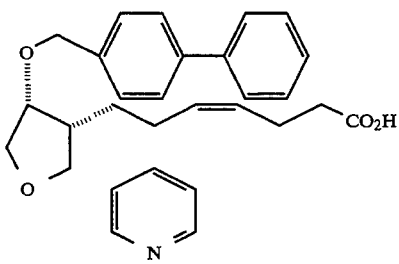

(IV)

or the dextrorotatory enantiomer thereof; or a pharmaceutically acceptable ester thereof; or a pharmaceutically acceptable salt thereof.

Further preferred are compounds of formula I wherein R is aryl-lower alkoxy or biaryl-lower alkoxy and the sum of m+n is 4; or a pharmaceutically acceptable ester thereof; or a pharmaceutically acceptable salt thereof.

A specific embodiment relates to compounds of the formula I wherein R is biphenylmethoxy; n is 2; m is 2; Y is vinylene; or a pharmaceutically acceptable ester thereof; or a pharmaceutically acceptable salt thereof.

A further specific embodiment relates to the dextrorotatory enantiomer of a compound of the formula I wherein R is biphenylmethoxy; n is 2; m is 2; Y is vinylene; or a pharmaceutically acceptable ester thereof; or a pharmaceutically acceptable salt thereof.

The term "lower" when referred to above and hereinafter in connection with organic groups, radicals or compounds respectively defines such with up to and including 7.

Lower alkyl preferably contains 1–7 carbon atoms and represents for example methyl, ethyl, propyl, isopropyl, n-butyl, sec-butyl, tert-butyl, pentyl, hexyl and heptyl radicals. $C_1$–$C_4$alkyl is preferred.

Lower alkoxy preferably contains 1–4 carbon atoms in the alkoxy portion and represents for example, methoxy, ethoxy, propoxy, isopropoxy, butoxy, isobutoxy and sec-and tert-butoxy.

Aryl represents preferably 1- or 2-naphthyl or phenyl, or said 1- or 2-naphthyl or phenyl substituted by one or more substituents selected from halogen, trifluoromethyl, hydroxy, lower alkyl-(thio, sulfinyl or sulfonyl), lower alkoxy, lower alkyl, nitro, azido, amino, cyano, carboxy or carboxy derivatized in the form of a pharmaceutically acceptable ester or amide. Further preferred aryl is phenyl.

Biaryl represents preferably biphenyl or biphenyl substituted by one or more substituents selected from halogen, trifluoromethyl, hydroxy, lower alkyl-(thio, sulfinyl or sulfonyl), lower alkoxy, lower alkyl, nitro, azido, amino, cyano, carboxy or carboxy derivatized in the form of a pharmaceutically acceptable ester or amide. Further preferred biaryl is biphenyl.

Cycloalkyl represents preferably $C_3$–$C_7$cycloalkyl.

A pharmaceutically acceptable ester advantageously represents a prodrug ester that may be convertible by solvolysis or under physiological conditions to the free carboxylic acid, e.g. lower alkyl; lower alkoxycarbonyl; (amino, mono- or di-lower alkylamino) substituted lower alkoxycarbonyl, carboxy-substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2.2.1]-heptyloxycarbonyl-substituted lower alkoxycarbonyl, especially bicyclo[2.2.1]-heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or 3-pyridyloxycarbonyl.

Preferred as prodrug esters are e.g. the lower alkyl, pivaloyloxymethyl, 2-diethylaminoethyl or bornyloxycarbonylmethyl esters. Lower alkyl esters are for example the methyl, ethyl, propyl, isopropyl, isobutyl and neopentyl esters.

Pharmaceutically acceptable salts are preferably metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or mono-, di- or tri-hydroxy-lower alkyl amines, e.g. methylamine, diethylamine, triethylamine, dicyclohexylamine, triethanolamine, ethylenediamine, or tris-(hydroxymethyl)methylamine. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of the invention exhibit valuable pharmacological properties, e.g. by selectively inhibiting thromboxane synthetase activity and blocking thromboxane receptor activity in mammals. The compounds are thus useful for treating disorders responsive to thromboxane synthetase inhibition and to thromboxane receptor antagonist activity in mammals, primarily cardiovascular disorders such as thrombosis, atherosclerosis, cerebral infarctions (strokes), myocardial infarctions (heart attacks), and other occlusive vascular conditions.

The novel compounds of the invention are active in state of the art in vitro and in vivo test systems, indicative of thromboxane receptor antagonist activity and thromboxane synthetase inhibitory activity.

The above-cited properties are demonstrable using in vitro and in vivo tests, using advantageously mammals, e.g. guinea pigs, rats, dogs, monkeys, rabbits or isolated organs, tissues and blood preparations thereof, as well as with human blood (e.g. platelet) preparations. Said compounds can be applied in vitro in the form of solutions, e.g. preferably aqueous solutions, and in vivo either enterally or parenterally, advantageously orally or intravenously, e.g. within gelatin capsules, as starch suspensions or in aqueous solutions. The dosage in vitro may range between about $10^{-5}$ molar and $10^{-9}$ molar concentrations, preferably between about $10^{-6}$ and $10^{-9}$ molar concentrations. The dosage in vivo may range between about 0.01 and 100 mg/kg/day, preferably between about 0.1 and 50 mg/kg/day, advantageously between about 0.1 and 30 mg/kg/day, depending on the compound and the route of administration.

The in vitro antagonism of thromboxane receptor activity can be demonstrated e.g. as described by Le Breton et al in Proc. Nat. Acad. Sci. 76, 4097 (1979).

The inhibition of thromboxane-$A_2$ receptor activity is determined by measuring the inhibition of U-46619 induced platelet aggregation of aspirinated human washed platelets and in human platelet rich plasma. U-46619 is (15S)-hydroxy-11-$\alpha$,9-$\alpha$(epoxymethanol)-prosta-(5Z,13E)-dienoic acid, a thromboxane-$A_2$ receptor agonist, as described by Di Minno et at, Thromb. Haemost. 45, 103 (1981).

Illustrative of the invention, the compound of Example 1 inhibits thromboxane-$A_2$ receptor activity in vitro with an $IC_{50}$ of $26.5 \times 10^{-9}$M as determined by inhibition of U-46619-induced aggregation of aspirinated washed human platelets; $IC_{50}$ for the compound of Example 8(a) is $28 \times 10^{-9}$M.

Further illustrative of the invention, the in vitro $IC_{50}$ for inhibition of U-46619 induced aggregation in platelet rich plasma is $2.5 \times 10^{-7}$M for the compound of Example 1 and about $4 \times 10^{-7}$M for the compound of Example 8(a).

Indicative of the beneficial effects, e.g. in occlusive cardiovascular disorders, the compounds of the invention inhibit variously experimentally induced platelet aggregation, e.g. platelet aggregation induced by collagen or U-46619. Such inhibition of platelet aggregation is determined using methodology known in the art, e.g. in vitro in the presence of a compound of the invention in human platelet rich plasma, or by measuring the inhibition of aggregation seen in plasma obtained from a mammal previously administered a compound of the invention, e.g. orally or intravenously when compared to controls. Platelet aggregation is measured in a Born aggregometer and platelet rich plasma is prepared from venous blood e.g. as described in Br. J. Haematol. 43, 637 (1979). Suitable test animals are anesthetized rats or guinea pigs and unanesthetized rabbits or cyanomolgus monkeys.

For example, the effect of the compounds of the invention in inhibiting platelet aggregation and reducing plasma levels of thromboxane can be determined as follows:

Anesthetized rats or guinea pigs are administered either the test compound or vehicle orally as a suspension in corn starch. Blood is withdrawn after 15 minutes to 1 hour, a small portion of which is incubated at 37° C. followed by radio-immunoassay to determine the serum level of thromboxane $B_2$. The major portion of the blood is processed to separate the plasma which is subjected to U-46619 or collagen-induced platelet aggregation assays mentioned but not described in detail.

Illustrative of the invention, the compound of Example 1 when given orally to conscious guinea pigs at a dose of 0.3 mg/kg effectively inhibits U46619-induced platelet aggregation 1 hour post dose; an oral dose of 0.23 mg/kg of the compound of Example 1 increases the concentration of thromboxane-mimetic required to induce 50% maximal aggregation by 50-fold.

The effect on plasma levels of thromboxane and prostacyclin can also be determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane $B_2$ and another aliquot for 6-keto-$PGF_{1\alpha}$, the stable metabolites of thromboxane $A_2$ and prostacyclin ($PGI_2$) respectively, by radioimmunoassay.

Further illustrative of the invention, the compound of Example 1 when given orally to cyanomolgus monkeys at a 30 mg/kg dose totally inhibited U46619-induced ex vivo platelet aggregation for at least 8 hours with a return to predose values at 24 hours; serum thromboxane $B_2$ was inhibited 24 hours with concomitant elevations of 6-keto-$PGF_{1\alpha}$ (the stable metabolite of $PGI_1$) and $PGE_2$ levels.

The pulmonary effects of the compounds of the invention can be demonstrated e.g. by measuring the inhibition of bronchoconstriction induced by arachidonic acid in the anesthetized guinea pig model as described in Br. J. Pharmacol. 30, 283–307 (1967).

Illustrative of the invention, the compound of Example 1 inhibits bronchoconstriction caused by prior administration of arachidonic acid (250 µg/kg i.v. followed by 2×500 µg/kg i.v.) with an $ED_{50}$ of about 6 µg/kg i.v.

The aforementioned thromboxane receptor antagonist and thromboxane synthesis inhibitory properties and resulting effects render the compounds of the invention particularly useful as therapeutic agents in mammals, e.g. for the treatment of occlusive vascular conditions and conditions of bronchoconstriction.

The compounds of the invention can be prepared using general processes comprising:

(a) for a compound of the formula I wherein Y is vinylene, condensing a compound of the formula V

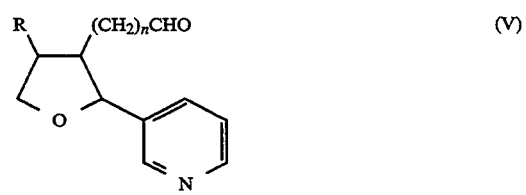

wherein R and n have meaning as previously defined, with a Wittig type reagent of the formula VI

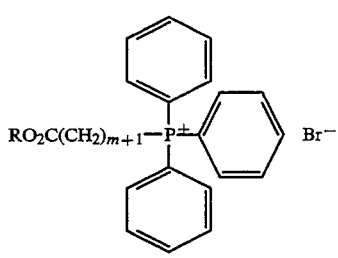

(VI)

wherein R represents e.g. lower alkyl, and m and n have meanings as previously defined;

(b) alternatively, for a compound of the formula I wherein Y is vinylene, reacting a compound of the formula VII

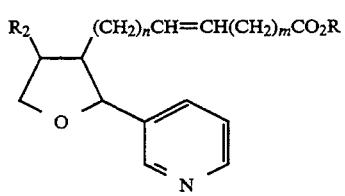

(VII)

wherein $R_2$ is a protected hydroxyl group e.g. tert-butyl dimethylsilyloxy with HCl gas and condensing the product with a compound R'X wherein X is a leaving group e.g. iodide and R' is aryl-lower alkyl, biaryl-lower alkyl, lower alkyl or cycloalkyl-lower alkyl;

(c) for a compound of the formula I wherein Y is ethylene, the double bond of the compound of formula VIII

(VIII)

can be hydrogenated. Art methods for addition of hydrogen across the double bond of an alkenoic acid include e.g. hydrogen addition in the presence of an active catalyst such as nickel, palladium or platinum at moderately elevated temperatures and pressures.

(d) for a compound of formula I wherein Y is methyleneoxy, condensing under basic conditions a compound of formula IX

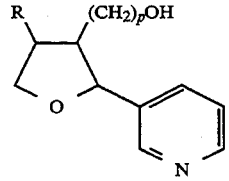

(IX)

wherein R has meaning as defined hereinabove and p is 1, 2, 3 or 4 with a compound of the formula X

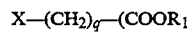

(X)

wherein X is a leaving group, q is 1, 2, 3 or 4 and $R_1$ is e.g. lower alkyl;

(e) alternatively, for a compound of formula I wherein Y is methyleneoxy, condensing under basic conditions a compound of formula XI

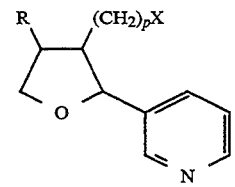

(XI)

wherein X is a leaving group and p is 1, 2, 3 or 4 with a compound of formula XII

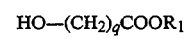

(XII)

wherein $R_1$ is e.g. lower alkyl and q is 1, 2, 3 or 4;

The reaction according to process (a) is carried out according to conditions well-known in the art for a Wittig type condensation of an aldehyde with a Wittig reagent. For example, the condensation with a triphenylphosphoranylidene derivative is carried out using a strong base, such as potassium t-butoxide in tetrahydrofuran so as to obtain the cis alkene as the predominant product.

The starting materials of formula V, IX and XI can be prepared from a compound of the formula XIII

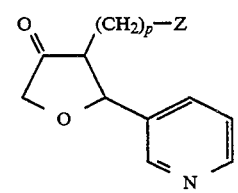

(XIII)

wherein Z is hydroxy in protected form and wherein p is as defined above, by (1) converting the ketone to the primary amine, e.g. via the oxime, and condensation thereof with a reactive derivative of an acylsulfonic acid and converting such to a starting material of formula V, IX or XI wherein R represents acylsulfonylamido; or (2) reducing a ketone of formula XIII to a corresponding 3-hydroxytetrahydrofuran derivative and condensing such with a reactive esterified derivative of an alcohol of the formula

(XIV)

wherein R' has meaning as previously defined (and removing protecting groups as required) to obtain an intermediate of formula XV

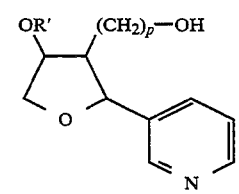

(XV)

wherein R' and p have meaning as defined above which can in turn be convened to a compound of formula V, IX or XI in which R represents OR'.

A 3-hydroxy-tetrahydrofuran precursor of the ketone intermediate XIII, e.g. of formula XVI

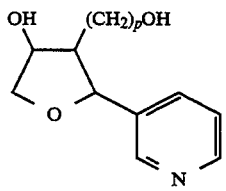 (XVI)

can be prepared by cyclizing a compound of formula XVII

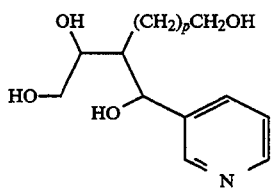 (XVII)

in which hydroxy groups not involved in the cyclization are in properly protected form, in the presence of a condensing agent such as triphenylphosphine and diethyl azodicarboxylate or p-toluenesulfonyl chloride in pyridine.

An intermediate of formula XVI in appropriately protected form can be converted to a corresponding intermediate of formula V and IX as described herein using standard methods of alkylation with R'OH and/or oxidation, e.g. by Swern oxidation using oxalyl dichloride, dimethyl sulfoxide and a tertiary amine to obtain a ketone or aldehyde. An intermediate of formula XVI can further be converted to starting materials of the formula XI by converting the primary hydroxyl group to a leaving group. Leaving groups include any group that is the conjugate base of a strong acid. Typically, leaving groups include halides, mesylates, benzenesulfonates, tosylates. The hydroxyl group is convened to a leaving group using standard methods for conversion of C—OH groups to C—leaving groups, e.g. reaction with HX, SOCl₂ and PCl₃ or p-toluene sulfonyl chloride.

An intermediate of formula XVII can in turn be prepared by reduction of a pyridyl ketone of the formula XVIII

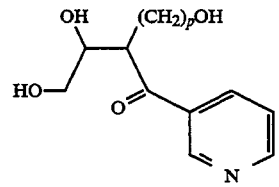 (XVIII)

in appropriately protected form, with a reducing agent such as sodium borohydride. A ketone of formula XVIII can in turn be prepared by condensation of 3-pyridyllithium with a lactone of the formula XIX

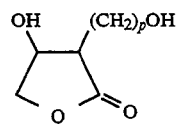 (XIX)

wherein hydroxy groups are suitably protected.

An intermediate of formula XIX can in turn be prepared by condensation of e.g. a compound of the formula XX

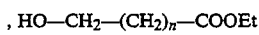 , HO—CH₂—(CH₂)ₙ—COOEt (XX)

wherein hydroxy group is protected e.g. as a benzyl derivative with the compound R₃OCH₂CHO, wherein R₃ is a protecting group, in the presence of a strong base, e.g. lithium diisopropylamide followed by hydrogenation with e.g. palladium over carbon.

An intermediate of the formula XX can be prepared by ring opening of an ω-lactone, e.g. δ-valerolactone, with e.g. potassium hydroxide, simultaneously protecting the resulting ω-hydroxy group as e.g. a benzyl derivative by condensing with benzyl chloride.

The starting materials of formula VII can be prepared from a compound of the formula XXI

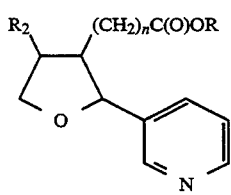 (XXI)

by converting the ester moiety to an aldehyde by
(1) hydrolyzing and converting to an amide e.g. by treating with N,O-dimethylhydroxylamine hydrochloride, 1-hydroxybenzotriazole monohydrate and 1-(3-dimethylaminopropyl)-3-ethylcarbodiimide hydrochloride followed by treatment with e.g. lithium aluminum hydride; or
(2) treating with e.g. diisopropylaluminum hydride and condensing the aldehyde with the compound of the formula VI.

The intermediate of the formula XXI, e.g. wherein n=2, can in turn be prepared from a compound of formula XXII

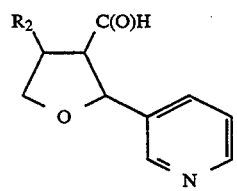 (XXII)

by treatment with methyl (triphenylphosphoranylidene) acetate followed by hydrogenattion e.g. over palladium on carbon catalyst.

The intermediate of formula XXII can in turn be prepared from a compound of the formula XXIII

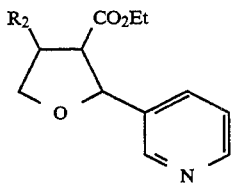

(XXIII)

wherein R₂ is a protected hydroxyl group, by converting the ester moiety to an aldehyde by
(1) hydrolyzing and converting to an amide e.g. by treating with N,O-dimethylhydroxylamine hydrochloride, 1-hydroxybenzotriazole monohydrate and 1-(3-dimethylaminopropyl)-3-ethylcarbodiimide hydrochloride followed by treatment with e.g. lithium aluminum hydride; or
(2) wearing with e.g. diisopropylaluminum hydride.

The intermediate of formula XXIII can in turn be prepared from a compound of the formula XXIV

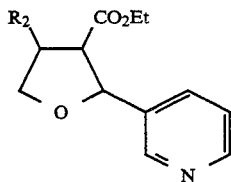

(XXIII)

by reduction e.g. with sodium borohydride followed by e.g. acetic acid-ethanol mixture.

The intermediate of formula XXIV can in turn be prepared from a compound of the formula XXV

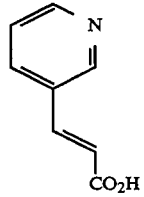

(XXV)

by esterifying with e.g. ethanol and treating with sodium ethoxide and ethyl glycolate.

In starting compounds and intermediates which are converted to the compounds of the invention in a manner described herein, functional groups present, such as carbonyl and hydroxy groups, are optionally protected by conventional protecting groups that are common in preparative organic chemistry. Protected carbonyl and hydroxy groups are those that can be converted under mild conditions into free carbonyl and hydroxy groups without the molecular framework being destroyed or other undesired side reactions taking place.

Well-known protecting groups that meet these conditions and their introduction and removal are described, for example, in J. F. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York 1965.

The compounds of the invention can be convened into each other according to conventional methods. Thus, for example, resulting esters may be hydrolyzed with aqueous alkalies, such as alkali metal carbonates or hydroxides. Resulting free acids may be esterified with e.g. said unsubstituted or substituted alkanols or reactive esterified derivatives thereof such as alkyl halides, or diazoalkanes. The compounds of the invention, when free acids, are also convened into metal or ammonium salts in conventional manner. The basic compounds of the invention are also converted to acid addition salts in conventional manner.

The compounds of the invention wherein Y is vinylene can be convened to compounds wherein Y is ethylene by addition of hydrogen across the double bond of the alkenoic acid using an active catalyst e.g. nickel, palladium or platinum.

Any resulting free acid or base can be converted into a corresponding metal, ammonium or acid addition salt respectively, by reacting it with an equivalent amount of the corresponding base, basic salt or ion exchange preparation.

In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or may be solvated by solvents used for the crystallization.

Depending on the choice of starting materials and methods, the new compounds may be in the form of one of the possible isomers or mixtures thereof, for example, as substantially pure geometric (Z or E, cis or trans) isomers, optical isomers (antipodes), racemates, or mixtures thereof. The aforesaid possible isomers or mixtures thereof are within the purview of this invention.

In case mixtures of geometric or optical isomers of the above compounds are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(α-methylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or elevated pressure.

The invention further includes any variant of said processes, in which an intermediate product obtainable at any stage of the process is used as a starting material and any remaining steps are carded out, or the process is discontinued at any stage thereof, or in which the starting materials are formed under the reaction conditions, or in which the reaction components are used in the form of their salts or optically pure antipodes.

Details concerning the preparation of the products of the invention, intermediates and starting materials are provided in the examples with respect to protecting groups, reagents and stereochemistry of the products obtained. Additional methods of preparation are also illustrated in the examples.

The present invention also relates to the use of the compounds of the invention for the preparation of pharmaceutical compositions especially pharmaceutical compositions having thromboxane suppressing, i.e. thromboxane synthetase inhibitory and thromboxane receptor blocking activity useful for the treatment or prevention of thromboxane dependent conditions or syndromes in mammals.

The pharmaceutical compositions according to the invention are those suitable for enteral, such as oral or rectal, transdermal and parenteral administration (including infusion) to mammals, including man, for the treatment or prevention of conditions or syndromes responsive to suppression of thromboxane activity, such as occlusive vascular conditions, comprising an effective thromboxane activity suppressing amount of a compound of the invention in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with 1) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therpeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The dosage of active compound administered is dependent on the species of warm-blooded animal (mammal), the body weight, age and individual condition, and on the form of administration.

The active ingredient is administered at an effective thromboxane activity suppressing dose, e.g. between about 0.01 to 50 mg/Kg/day, preferably between about 0.1 to 30 mg/Kg/day orally, between 0.1 to 10 mg/Kg/hour by infusion, and between 0.01 to 5 mg/Kg intravenously.

A unit dosage for oral administration to a mammal of about 50 to 70 Kg may advantageously contain between about 25 and 250 mg of the active ingredient.

The pharmaceutical formulations contain an effective thromboxane activity suppressing amount of a compound of the invention as defined above either alone or in combination with another therapeutic agent selected from e.g. a thrombolytic agent, an angiotensin converting enzyme inhibitor, a calcium channel blocker, an anticoagulant, a serotonin-2-antagonist, or an immunosuppressive agent at an effective therapeutic dose. Such therapeutic agents and their effective doses are well-known in the art.

Illustrative thrombolytic agents are e.g. TPA, urokinase, streptokinase, APSAC; illustrative angiotensin converting enzyme inhibitors are e.g. captopril, enalapril, enalaprilat, quinapril, ramipril, cilazapril, delapril, fosenopril, zofenopril, indolapril, lisinopril, moveltipril, perindopril, spirapril, pentopril, pivopril, benazepril, benazeprilat and libenzapril; illustrative calcium channel blockers are e.g. diltiazem, amlodipine, nifedipine, nisoldipine, verapamil, isradipine and felodipine; illustrative serotonin-2 antagonists are e.g. ketanserin, cinansenn, irindalone; illustrative anticoagulants are heparin, hirudin and derivatives thereof such as desulfatohirudin; and illustrative immunosuppressive agents are e.g. cyclosporine and related compounds.

The invention also further relates to the treatment of mammals, including man, using a compound of the invention, preferably in the form of a pharmaceutical composition, either alone or in combination with other therapeutic agents as illustrated herein.

More particularly the invention relates to:

(a) a method of suppressing thromboxane activity in mammals which comprises administering to a mammal in need thereof an effective thromboxane suppressing amount of a compound of the invention;

(b) a method of inhibiting thromboxane synthesis in mammals which comprises administering to a mammal in need thereof an effective thromboxane synthetase inhibiting amount of a compound of the invention;

(c) a method of blocking thromboxane receptor activity in mammals which comprises administering to a mammal in need thereof an effective thromboxane receptor blocking amount of a compound of the invention;

(d) a method of inhibiting platelet aggregation in mammals which comprises administering to a mammal in need thereof an effective platelet aggregation inhibiting amount of a compound of the invention;

(e) a method of treating or preventing thromboxane dependent conditions or syndromes in mammals which comprises administering to a mammal in need thereof an effective thromboxane activity suppressing amount of a compound of the invention.

Thromboxane dependent conditions or syndromes involved are e.g. myocardial infarctions (heart attacks); cerebral infarctions (strokes); angina (stable or unstable); hypertension such as pregnancy induced hypertension (e.g. toxemia, preeclampsia); renal disorders (e.g. lupus nephritis, diabetic nephropathy and cyclosporine-induced nephrotoxicity); peripheral vascular disorders (e.g. peripheral venous or arterial occlusive conditions); vascular e.g. coronary reocclusion after thrombolytic therapy, bypass surgery or angioplasty; allograft rejection as in heart transplantation; pulmonary disorders such as bronchoconstriction as in bronchial asthma; or platelet loss during extracorporeal circulation.

A particular aspect involves a method of treating or preventing occlusive vascular conditions comprising peripheral vascular disorders, thrombosis, atherosclerosis, cerebral and myocardial infarction, and coronary reocclusion occurring after angioplasty, after coronary bypass surgery or after thrombolytic therapy, which comprises administering to a mammal in need thereof an effective amount of a compound of the invention.

A further aspect of the invention relates to the treatment of disorders and syndromes described herein which comprises administering the compounds of the invention in conjunction with other therapeutic agents to mammals in order to enhance the therapeutic effectiveness of such other therapeutic agents.

For instance, the compounds of the invention can be administered to mammals to enhance the effect of thrombolytic agents (e.g. TPA, urokinase, streptokinase, anistreplase and the like), e.g. by reducing their required dose and the required time to achieve reperfusion in myocardial infarction, and also to prevent or reduce the incidence of reocclusion after treatment with said thrombolytic agents.

Thus the present invention provides a method for the treatment of myocardial infarction and coronary occlusion in mammals comprising the administration, in combination with a said thrombolytic agent, of a compound of the invention which serves to reduce the dose of thrombolytic agent needed to lyse clots, to reduce the time required for lysis of clots, to prevent reocclusion following thrombolysis with the thrombolytic agent, and to keep blood vessels unobstructed for a longer period of time.

The compounds of the invention can also be administered to mammals at doses which are essentially devoid of antihypertensive activity to enhance the antihypertensive effect of angiotensin converting enzyme inhibitors, e.g. those cited hereinabove.

Similarly the compounds of the invention can also be administered to mammals to enhance the cardiovascular effects, e.g. antianginal effects, of calcium channel blockers (e.g. diltiazem, amlodipine, nifedipine, nisoldipine, verapamil, felodipine, isradipine) in the treatment of myocardial infarctions.

Further illustrative of the invention, the compounds of the invention can also be administered to mammals to enhance the effect of anticoagulants, e.g. a heparin, hirudin, desulfatohirudin, and derivatives thereof, to improve perfusion in occlusive vascular disorders.

Illustrative of the invention, the compounds of the invention can further be administered to mammals to enhance the antiplatelet effects of serotonin-2 receptor antagonists (e.g. ketanserin, cinanserin, irindalone) in the treatment of occlusive vascular disorders.

A further aspect of the invention comprises a method of alleviating cyclosporin-induced nephrotoxicity by administering to a mammal undergoing cyclosporine therapy an effective thromboxane suppressing amount of a compound of the invention.

In the above-cited methods of treatment in conjunction with another active ingredient, a compound of the invention may be administered either simultaneously, before of after the other active ingredient, either separately by the same or different route of administration or together in the same pharmaceutical formulation, in an amount effective for suppressing thromboxane activity.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Unless otherwise specified, chromatography is carded out using silica gel. Flash chromatography refers to medium pressure column chromatography according to Still et at, J. Org. Chem. 43, 2928 (1978).

EXAMPLE 1

A solution of 28.2 g (0.0597 mol) of methyl (Z)-(2S,3S,4R)-7-[4-(1,1'-biphenyl-4-ylmethoxy)-2-(3-pyridyl)tetrahydrofuran-3-yl]-4-heptenoate, 433 ml of methanol and 172.8 ml (0.173 mmol) of 1N sodium hydroxide is stirred at 45° C. for two h and at room temperature for 1½ h. The solvent is evaporated, the residue is taken up in water and extracted twice with ethyl ether. The aqueous layer is adjusted to pH 5.5 and extracted with ethyl acetate (3×10 ml). The combined extracts are washed with brine, dried (MgSO4), evaporated and the residue is crystallized from methylene chloride and ether to give (Z)-(2S,3S,4R)-7-[4-(1,1'-biphenyl-4-ylmethoxy)-2-(3-pyridyl)tetrahydrofuran-3-yl]-4-heptenoic acid, having mp. 96°–98° C. and $[\alpha]_D25 = +98.58$ (MeOH).

The starting material is prepared as follows:

A mixture of 100 g of δ-valerolactone, 50 ml of water, 350 ml of toluene, 280g of potassium hydroxide pellets and 300 ml of benzyl chloride is refluxed overnight with mechanical stirring and azeotroping the water with the use of a Dean-Stark apparatus. The thick white mass is cooled to room temperature and dissolved in 1 l of cold water. The organic layer is separated and the aqueous layer is condensed to ⅓ by heating over a period of 5 h. The mixture is cooled to room temperature, acidified with concentrated hydrochloric acid and extracted with ethyl acetate (2×300 ml). The combined extracts are washed with brine, dried (MgSO$_4$) and evaporated to dryness to give 5-benzyloxypentanoic acid.

A mixture of 61.1 g of 5-benzyloxypentanoic acid, 566 ml of ethanol and 10 ml of concentrated sulfuric acid is refluxed for 15 h. The mixture is cooled to room temperature, 10 ml of triethylamine are added and evaporated. The residue is diluted with 250 ml of ether and the solution is washed in water and brine dried (MgSO$_4$) and evaporated. The residual oil is distilled to give ethyl 5-benzyloxypentanoate, b.p. 110°–113° C. (0.7 mm/Hg).

A solution of 33.93 g of ethyl glycolate, 62.7 g of t-butyldimethylchlorosilane and 58.5 g of imidazole in 150 ml of dimethylformamide is stirred at room temperature for 15 h. The mixture is diluted with ether and washed with water (2×100 ml), brine, dried (MgSO$_4$) and evaporated. The residue is distilled to give ethyl t-butyldimethylsilyloxyacetate, b.p. 100°–105° C. (14 mm/Hg).

To a solution of 32.7g (0.15 mole) of ethyl t-butyldimethylsilyloxyacetate in 924 ml of methylene chloride a solution of 1M diisopropylaluminum hydride in methylene chloride is added dropwise with stirring at −78° C. over a period of ½ h. The mixture is stirred for 45 min and 100 ml of methanol is added dropwise. The mixture is diluted with 3 l of ether, 100 ml of brine and 70 g of sodium sulfate are added and the mixture is stirred at room temperature for 15 h. The solids are filtered, the filtrates are evaporated and the residue is distilled to give t-butyldimethylsilyloxyacetaldehyde, b.p. 65°–75° C. (14 mm/Hg).

To a solution of 20.4 g (0.201 mole) of diisopropylamine in 250 ml of tetrahydrofurane is added dropwise 100.2 ml (0.201 mole) of 2.01M solution of n-butyllithium in hexane with stirring at 0° C. The solution is cooled to −78° C. and a solution of 40.56 g (0.182 mole) of ethyl 5-benzyloxypentanoate in 30 ml of tetrahydrofurane is added dropwise over a period of ½ h. The mixture is stirred at −78° C. for another ½ h and a solution of 33.5 g (0.192 mole) of t-butyldimethylsilyloxyacetaldehyde in 20 ml of tetrahydrofurane is added dropwise. The mixture is stirred at −78° C. for 1 h and 12.1 ml of acetic acid is added dropwise. The mixture is warmed to 0° C., diluted with 250 ml of ether and 250 ml of ethyl acetate and washed with water. The organic layer is evaporated, the residue is diluted with 322 ml of methanol and the solution is treated with 43.1 ml of concentrated hydrochloric acid with stirring for 20 h. The mixture is evaporated and the residue is extracted with ethyl acetate. The extracts are washed with water and brine, dried (MgSO$_4$) and evaporated to give an oil which is then purified by flash chromatography using methylene chloride-ethyl acetate (4:1) as the eluent to obtain 2-(3-benzyloxy-propyl)-3-hydroxy-γ-butyrolactone as an oil.

A solution of 18.7 g of 2-(3-benzyloxypropyl)-3-hydroxy-γ-butyrolactone in 90 ml of ethanol-acetic acid (2:1) is hydrogenated over 640 mg of 10% palladium on carbon at 45 psi for 20 h. The catalyst is filtered and the filtrates are evaporated to give 2-(3-hydroxypropyl)-3-hydroxy-γ-butyrolactone as an oil.

To a solution of 11.8 g (0.074 mole) of 2-(3-hydroxypropyl)-3-hydroxy-γ-butyrolactone in 30 ml of methylene chloride are added 23.17 g (0.179 mole) of diisopropylethyl amine and 22.3 g (0.179 mol) of 2-methoxyethoxymethyl chloride. The mixture is stirred at room temperature for ½ h and at 45° C. for another 24 h and evaporated. The residue is taken up in ethyl acetate and washed with water and brine, dried (MgSO$_4$) and evaporated. The residue is purified by flash chromatography using methylene chloride-ethyl acetate (4:1) as eluent to give 2-[3-(2-methoxyethoxymethoxy)propyl]-2-(2-methoxyethoxymethoxy)-γ-butyrolactone as an oil.

A solution of 18.96 g (0.12 mole) of 3-bromopyridine in 50 ml of ether is added dropwise into a 54.72 ml (0.11 mole) of 2.01M n-butyllithium in hexane in 550 ml of ether at −78° C. with stirring under argon over a period of 20 min. The mixture is stirred for another ½ h and a solution of 30.35 g (0.0902 mole) of 2-[3-(2-methoxyethoxymethoxy)propyl]-2-(2-methoxyethoxymethoxy)-γ-butyrolactone in 30 ml of ether is added dropwise over a period of 10 min. The mixture is stirred at −78° C. for 2 h, allowed to warm up to −20° C., quenched with 15 ml of saturated aqueous ammonium chloride and washed with water and brine. The ether layer is dried (MgSO$_4$) and evaporated to give 2,5-bis-(2-methoxyethoxymethoxy)-3-nicotinoyl-hexan-1-one as an oil.

To a solution of 20.4 g (0.049 mole) of 2,5-bis-(2-methoxyethoxymethoxy)-3-nicotinoylhexan-1-one in 248 ml of ethanol 1.8 g (0.049 mole) of sodium borohydride is added in portions at room temperature, the mixture is stirred for 15 h and evaporated. The residue is triturated with methylene chloride, the solution is dried (MgSO$_4$) and evaporated. The residue is purified by flash chromatography using methylene chloride-methanol-ammonium hydroxide (300:25:1) to give 2,5-bis-(2-methoxyethoxy-methoxy)-3-[α-hydroxy-(3-pyridyl)methyl]-hexan-1-ol as an oil.

To a solution of 8.59 g (0.0205 mole) of 2,5-bis-(2-methoxyethoxymethoxy)-3-[α-hydroxy-(3-pyridyl)methyl]hexan-1-ol and 5.88 g (0.022 mole) of triphenylphosphine in 40.6 ml of methylene chloride a solution of 5 g (0.028 mole) of diethyl azodicarboxylate in 19 ml of methylene chloride is added dropwise at 0° C. with stirring under nitrogen over a period of 15 min. The mixture is stirred at 0° C. for another ½ h and evaporated. The residue is triturated with 10 ml of ether and the solution is allowed to stand at 4° C. overnight. The precipitated triphenylphosphine oxide is filtered off and washed with a small amount of ether. The combined filtrates are evaporated, the residue is dissolved in 50 ml of methanol and 10 ml of concentrated hydrochloric acid and the mixture is heated at 60° C. for 2 h. The solution is evaporated to a small volume, diluted with 15 ml of distilled water and the solution is extracted with ethyl acetate (2×10 ml). The aqueous layer is evaporated and the residue is dried under high vacuum to give 4-hydroxy-3-(3-hydroxyprop-1-yl)-2-(3-pyridyl)tetrahydrofuran hydrochloride as a thick viscous oil.

A solution of 10 g (0.0448 mole) of 4-hydroxy-3-(3-hydroxyprop-1-yl)-2-(3-pyridyl)tetrahydrofuran hydrochloride, 7.68 g (0.048 mole) of t-butyldimethylsilyl chloride and 6.86 g (0.0977 mole) of imidazole in 105.8 ml of dimethylformamide is stirred at room temperature for 15 h and evaporated. The residue is triturated with ethyl acetate and washed with water and brine, dried (MgSO$_4$) and evaporated. The residue is purified by flash chromatography using methylene chloride-ethyl acetate-methanol (20:4:1) to give 3-(3-t-butyldimethylsilyloxyprop-1-yl)-4-hydroxy-2-(3-pyridyl)tetrahydrofuran as an oil.

To a solution of 5.03 g (0.0397 mole) of oxalyl chloride in 23 ml of methylene chloride a solution of 5.6 g (0.0718 mole) of dimethyl sulfoxide in 23 ml of methylene chloride is added dropwise under nitrogen at −60° C. with stirring over a period of 15 min. The mixture is stirred at −70° C. for another 15 min and a solution of 8.5 g (0.0252 mole) of 3-(3-t-butyldimethylsilyloxyprop-1-yl)-4-hydroxy-2-(3-pyridyl)tetrahydrofuran in 31 ml of methylene chloride is added dropwise at −70° C. The mixture is stirred at −70° C. for 1 h and 25 ml of diisopropylethylamine are added at once. The mixture is warmed to room temperature and stirred for 40 min, washed with water, dried (MgSO$_4$) and evaporated. The residue is dissolved in 100 ml of methanol, 100 mg of sodium methoxide is added, the mixture is stirred at room temperature overnight and evaporated. The residue is purified by flash chromatography using methylene chloride-ethyl acetate-methanol (800:173:27) as eluent to give (2α,3β)-3-(t-butyldimethylsilyloxyprop-1-yl)-2-(3-pyridyl)tetrahydrofuran-4-one as an oil.

To a solution of 6.09 g (0.0182 mole) of (2α,3β)-3-(3-t-butyldimethylsilyloxyprop-1-yl)-2-(3-pyridyl)tetrahydrofuran-4-one in 48 ml of acetic acid-ethanol (9:1), 2.75 g (0.0728 mole) of sodium borohydride is added in portions with stirring at 0° C. over a period of 20 min. The mixture is stirred at 0° C. for another 2 h and evaporated. The residue is triturated with ethyl acetate and washed with concentrated aqueous sodium bicarbonate. The bicarbonate washings are extracted with ethyl acetate and the combined ethyl acetate extracts are dried (MgSO$_4$) and evaporated. The residue is purified by flash chromatography by using methylene chloride-methanol-ammonium hydroxide (300:25:1) as eluent to give (2α,3β,4α)-3-(3-t-butyldimethylsilyloxyprop-1-yl)-4-hydroxy-2-(3-pyridyl)tetrahydrofuran as an oil.

To a solution of 2.76 g (0.00818 mole) of (2α,3β,4α)-3-(3-t-butyldimethylsilyloxyprop-1-yl)-4-hydroxy-2-(3-pyridyl)tetrahydrofurane, 3.86 g (0.0147 mole) of triphenylphosphine, 0.67 g (0.0147 mole) of formic acid in 28 ml of tetrahydrofurane, is added dropwise 2.57 g (0.00147 mole) of diethyl azodicarboxylate over a period of 3 min. The mixture is stirred at room temperature for 1 h and evaporated. The residue is triturated with ether and the mixture is stirred at 0° C. for 1 h. The precipitated triphenylphosphine oxide is filtered and the filtrates evaporated. The residue is dissolved in 43 ml of methanol, 12 ml (0.012 mole) of 1N sodium hydroxide are added and the mixture is stirred at room temperature for 1.5 h and evaporated. The residue is triturated with water and extracted with ethyl acetate (3×30 ml). The combined extracts are dried (MgSO$_4$) and evaporated. The residue is purified by flash chromatography using methylene chloride-methanol-ammonium hydroxide (300:25:1) as eluent to give (2α,3β,4β)-3-(3-t-butyldimethylsilyloxyprop-1-yl)-4-hydroxy-2-(3-pyridyl)tetrahydrofuran as an oil.

A solution of 2.43 g (0.0072 mole) of (2α,3β,4β)-3-(3-t-butyldimethylsilyloxyprop-1-yl)-4-hydroxy-2-(3-pyridyl)tetrahydrofuran, 1.38 g (0.0083 mole) of (R)-(−)-a-methoxy-phenylacetic acid, 1.01 g (0.0083 mole) of 4-dimethylaminopyridine and 1.71 g (0.0083 mole) of dicyclohexylcarbodiimide in 24 ml of methylene chloride is stirred at room temperature for 1 h, filtered and evaporated. The residue is subjected to flash chromatography using ethyl acetate-methylene chloride (1:1) as eluent to give the less polar diastereomer (2S,3S,4R)-3-(3-t-butyldimethylsilyloxyprop-1-yl)-4-[(R)-(−)-a-methoxyphenylacetoxy-2-(3-pyridyl)tetrahydrofuran and the more polar diastereomer (2R,3R,4S)-3-(3-t-butyldimethylsilyloxyprop-1-yl)-4-[(R)-(−)-a-methoxy phenylacetoxy]-2-(3-pyridyl)tetrahydrofuran as oils.

A solution of 2.02 g (0.00416 mole) of (2S,3S,4R)-3-(3-t-butyldimethylsilyloxyprop-1-yl)-4-[(R)-(−)-a-methoxyphenylacetoxy)-2-(3-pyridyl)tetrahydrofuran, 8.32 ml (0.00832 mole) of 1N sodium hydroxide in 20 ml of methanol is stirred at room temperature for 1 h and evaporated. The residue is triturated with water and extracted with ethyl acetate (3×20 ml). The combined extracts are washed with water and brine, dried (MgSO$_4$) and evaporated. The residue is purified by flash chromatography to give (2S,3S,4R)-3-(3-t-butyldimethylsilyloxyprop-1-yl)-4-hydroxy-2-(3-pyridyl)tetrahydrofuran as an oil with [α]D$_{25}$=+43.8 (MeOH).

A 0.694 g (0.00346 mole) suspension of 20% potassium hydride in mineral oil is washed twice with petroleum ether and resuspended in 5 ml of tetrahydrofuran. The suspension is cooled with stirring at −15° C. and a solution of 1.169 g (0.00346 mole) of (2S,3S,4R)-3-(3-t-butyldimethylsilyloxyprop-1-yl)-4-hydroxy-2-(3-pyridyl)tetrahydrofurane in 10 ml of tetrahydrofurane is added dropwise. After stirring the mixture for 2 min, 1.37 g (0.00346 mole) of 4-iodomethylbiphenyl is added at once and the mixture is stirred at −15° C. for 75 min.

Concentrated ammonium chloride is added and the mixture is extracted with ether (2×20 ml). The combined extracts are washed with water and brine, dried (MgSO$_4$) and evaporated. The residue is purified by flash chromatography using ethyl acetate-methylene chloride ( 1:1) to give (2S,3S,4R)-4-(biphenyl-4-ylmethoxy)-3-(3-t-butyldimethylsilyloxyprop-1-yl)-2-(3-pyridyl)tetrahydrofuran as an oil having [α]$_D^{25}$= +71.99 MeOH).

To a solution of 1.37 g (0.00272 mole) of (2S,3S,4R)-4-(biphenyl-4-ylmethoxy)-3-(3-t-butyldimethylsilyloxyprop-1-yl)-2-(3-pyridyl)tetrahydrofuran in 14 ml of methanol, hydrogen chloride gas is bubbled until the pH of the solution is brought to 3. The mixture is stirred at room temperature for 1 h and evaporated. The residue is triturated with ethyl acetate and neutralized with concentrated aqueous sodium bicarbonate. The aqueous layer is extracted once more with ethyl acetate and the combined organic extracts are dried (MgSO$_4$) and evaporated. The residue is purified by flash chromatography using methylene chloride-methanol-ammonium hydroxide (300:25:1) as eluent to give (2S,3S,4R)-4-(biphenyl-4-ylmethoxy)-3-(3-hydroxyprop-1-yl)-2-(3-pyridyl)tetrahydrofuran as an oil having [α]$_D^{25}$=+89.78° (MeOH).

To a solution of 0.48 g (0.00383 mole) of oxalyl chloride in 7 ml of methylene chloride is added dropwise a solution of 0.54 g (0.0067 mole) of dimethylsulfoxide in 4 ml of dichloromethane with stirring at −60° C. After stirring the mixture for another 10 min at −70° C., a solution of 0.95 g (0.00244 mole) of (2S,3S,4R)-4-(biphenyl)-4-ylmethoxy)-3-(3-hydroxyprop-1-yl)-2-(3-pyridyl)tetrahydrofuran in 8 ml of dichloromethane is added dropwise over a period of 10 min. The mixture is stirred at −70° C. for 1 h and 2.48 ml (0.014 mole) of diisopropylethyl amine are added at once. The mixture is allowed to warm up to room temperature, washed with water and brine, dried (MgSO$_4$) and evaporated. The residue is purified by flash chromatography using methylene chloride-methanol-ammonium hydroxide (300:25:1) as eluent to give (2S,3S,4R)-3-[4-(biphenyl-4-ylmethoxy)-2-(3-pyridyl)tetrahydrofuran-3-yl]propanal as oil.

To a suspension of 1.34 g (0.003 mole) of (3-carbomethoxypropyl)triphenylphosphonium bromide (prepared from methyl 4-bromobutyrate and triphenyl phosphine in refluxing toluene and recrystallizing the product from 2-propanol, mp 204°–205° C.) in 5.5 ml of tetrahydrofurane is added dropwise 2.57 ml (0.00257 mole) of a one molar solution of potassium tert-butoxide in tetrahydrofurane with stirring at 0° C. The mixture is stirred at 0° C. for another 45 min and a solution of 584 mg (0.00151 mole) of (2S,3S,4R)-3-[4-(biphenyl-4-ylmethoxy)-2-(3-pyridyl)tetrahydrofuran-3-yl]propanl in 2 ml of tetrahydrofurane is added dropwise over a period of 5 min. The mixture is stirred at 0° C. for 1 h, quenched with 2.5 ml of concentrated aqueous ammonium chloride and diluted with ether. The mixture is washed with water (2×10 ml) and brine, dried (MgSO$_4$) and evaporated. The residue is purified by flash chromatography using methylene chloride-ethyl acetate-methanol (20:4:1) as eluent to give (Z)-(2S,3S,4R)-7-[4-(biphenyl-4-ylmethoxy)-2-(3-pyridyl)-tetrahydrofuran-3-yl]hept-4-enoic acid methyl ester as an oil having [α]$_D^{25}$=+70.11° (MeOH).

EXAMPLE 2

Alternatively, the starting material in Example 1 is prepared as follows:

To a stirred suspension of 150 g of β-(3-pyridyl)acrylic acid in 1500 ml of ethanol a slow stream of hydrogen chloride gas is bubbled for 4 to 5 hr, where all solids dissolved. Approximately 500 ml of ethanol are distilled off at atmospheric pressure, the residual solution is cooled and diluted with 1500 ml of ether with stirring. The solids are filtered, washed with ether and resuspended in ethyl acetate. The stirred suspension is neutralized with conc. aq. sodium bicarbonate. The ethyl acetate layer is separated and the aqueous layer is extracted once more with ethyl acetate. The combined organic extracts are washed with brine, dried (MgSO$_4$), evaporated and the residual oil is distilled to give 110 g of ethyl β-(3-pyridyl)acrylate with bp 95°–100° C., 0.1 mm/Hg.

To a solution of sodium ethoxide, prepared by dissolving 36.11 g (1.57 mol) of sodium in 300 ml of absolute ethanol, cooling to room temperature and adding with stirring 600 ml of dry tetrahydrofurane, 217.98 g (2.092 mol) of ethyl glycolate was added at 0° C. with stirring under argon. The mixture is stirred for 2 min. To the resulting suspension is added 185.3 g (1.046 mol) of ethyl β-(3-pyridyl) acrylate and the mixture is stirred at 50° C. for 48 h and at room temperature an additional 4 days. The mixture is evaporated at aspirator pressure, the residue is diluted with 250 ml of water and 250 ml of brine and extracted twice with ethyl acetate. The aqueous layer is acidified to pH 5.5 with conc. hydrochloric acid and extracted with ethyl acetate (4×100 ml). The combined acidic ethyl acetate extracts are dried (MgSO$_4$) and evaporated to give 182 g of 3-carboethoxy-2-(3-pyridyl)tetrahydrofuran-4-one as an oil having a mass spectrum m/z 236 (M+1) (calcd. MW 235.24).

A solution of 23.5 g (0.1 mol) of 3-carboethoxy-2-(3-pyridyl)tetrahydrofuran-4-one in 20 ml of ethanol is added dropwise to a stirred solution of 15.2 g (0.4 mol) of sodium borohydride in 1000 ml of ethanol at −70° C. over a period of 30 min. The mixture is stirred at −70° C. for another 10 min and a mixture of 100 ml of acetic acid-ethanol (1:4 v/v) is added dropwise over a period of 1 h. The mixture is allowed to warm up to −30° C., 20 ml of acetone is added and the mixture is evaporated to dryness at aspirator pressure. The residue is triturated with 500 ml of methylene chloride and the solution is washed with water and brine. The aqueous layers are back extracted with methylene chloride. The combined methylene chloride extracts are dried (MgSO$_4$) and evaporated to give 19.5 g of (2β,3α,4β)-3-carboethoxy-4-hydroxy-2-(3-pyridyl)tetrahydrofurane contaminated with a small amount of the isomer (2β,3α,4α)-3-carboethoxy-4-hydroxy-2-(3-pyridyl)tetrahydrofurane with elemental analysis: C,60.43; H,6.30; N,5.89 (theory: C,60.75, H,6.37; N,5.9).

A mixture of 19.8 g (0.083 mol) of (2β,3α,4β)-3-carboethoxy-4-hydroxy-2-(3-pyridyl)tetra-hydrofurane, 43.7 ml of N,N-dimethylformamide, 16.29 g (0.104 mol) of t-butyldimethylsilyl chloride and 15.35 g (0.158 mol) of imidazole is stirred at room temperature overnight. The mixture is diluted with water and extracted with ether (2×). The ether extracts are washed with water and brine, dried (MgSO$_4$) and evaporated to give an oil which is purified by flash chromatography from silica gel (8×30 cm$^2$) using methylene chloride-ethyl acetate (1:1) as eluent to give 32.7 g of the less polar isomer (2β,3α,4β)-3-carboethoxy-4-(t-butyldimethylsilyloxy)-2-(3-pyridyl)tetrahydrofurane as an oil having elemental analyses: C,60.80; H, 7.99; N, 4.83 (theory: C, 61.50; H, 8.31; N, 3.98) and a mass spectrum m/z 352 (M+1) (calcd. MW 351.53), and 4.5 g of the more polar isomer (2β,3α,4α)-3-carboethoxy-4-(t-butyldimethylsilyloxy)-2-(3-pyridyl)tetrahydrofurane as an oil with elemental analysis: C, 61.41; H, 8.26; N, 4.23 and having a mass spectrum of m/z 352 (M+1).

To a solution of 126.46 g (0.36 mol) of (2β,3α,4β)-3-carboethoxy-4-(t-butyldimethylsilyloxy)-2-(3-pyridyl)-tetrahydrofurane in 770 ml of methanol is added 385 ml (0.385 mol) of 1N aq. sodium hydroxide, dropwise at 0° C. with stirring. The mixture is stirred at room temperature overnight and evaporated at aspirator pressure. The residue is diluted with water and extracted with ether (2×). The ether extracts are discarded. The aqueous layer is diluted with 500 ml of methylene chloride. The mixture is cooled with stirring to 0° C. and the pH of the aqueous layer is adjusted to 5.5 by dropwise addition of 2N aqueous hydrochloric acid. The methylene chloride layer is separated, the aqueous layer is extracted with methylene chloride (2×) and the combined organic extracts are washed with brine, dried (MgSO4) and evaporated to give a crystalline residue. Recrystallization from ethyl acetate gave 64.5 g of (2β,3α,4β)-4-(t-butyldimethylsilyloxy)-2-(3-pyridyl)-tetrahydrofuran-3-carboxylic acid having mp 132°–134° C. with elemental analysis: C, 59.11; H, 7.79; N, 4.20 (Theory: C, 59.41; H, 7.70; N,4.33).

To a solution of 65.43 g (0.2 mol) of (2β,3α,4β)-4-(t-butyldimethylsilyloxy)-2-(3-pyridyl)-tetrahydrofuran-3-carboxylic acid in 645 ml of hot ethyl acetate, 24.5 g (26.1 ml, 0.2 mol) of 1-(−)-α-methylbenzylamine is added and the mixture is allowed to stand at room temperature overnight. The precipitated solids are filtered and washed with ethyl acetate. The solids are recrystalized two times from ethyl acetate to give 33.3 g (2S,3S,4S)-4-(t-butyldimethylsilyloxy)-2-(3-pyridyl)tetrahydrofuran-3-carboxylic acid, 1-(−)-α-methylbenzylamine addition salt having mp 141.5°–143.5° C. and optical rotation [α]$_D$25= +6.89 (C=8.65 mg/ml, methanol).

(2S,3S,4S)-4-(t-Butyldimethylsilyoxy)-2-(3-pyridyl)-tetrahydrofuran-3-carboxylic acid, 1-(−)-α-methylbenzylamine addition salt (33.5 g, 0.0754 mol) is dissolved in 745 ml (0.745 mol) of 1N sodium hydroxide and the solution is extracted with ethyl acetate (3×). The aqueous solution is diluted with 150 ml of methylene chloride. The mixture is cooled to 0° C. and the pH of the aqueous layer is adjusted to 5.5 with stirring and dropwise addition of 2N aqueous hydrochloric acid. The layers are separated and the aqueous layer is extracted with methylene chloride (2×). The combined methylene chloride extracts are washed with brine, dried (MgSO4) and evaporated to a small volume to give on dilution with ether, 21.15 g of (2S,3S,4S)-4-(t-butyldimethylsilyloxy)-2-(3-pyridyl)tetrahydrofuran-3-carboxylic acid, having mp 130°–132° C. and optical rotation [α]$_D$25= +9.40 (methanol).

To a solution of 10 g (0.0309 mol) of (2S,3S,4S)-4-(t-butyldimethylsilyloxy)-2-(3-pyridyl)-tetrahydrofuran-3-carboxylic acid in 222 ml of methylene chloride are added with stirring 3.62 g (0.037 mol) of N,O-dimethylhydroxylamine hydrochloride, 6.27 g (0.041 mol) of 1-hydroxybenzotriazole monohydrate, 11.86 g (0.0619 mol) of 1-(3-dimethylaminopropyl)-3-ethylcarbodiimide hydrochloride and 3.75 g (5.17 ml, 0.0371 mol) of triethylamine, the mixture is stirred at room temperature overnight and evaporated. The residue is triturated with ether and washed twice with water. The aqueous layers are back extracted with ether and the combined ether extracts are washed twice with 10% aqueous potassium carbonate, once with brine then dried (MgSO4) and evaporated to give 10.76 g of (2S,3S,4S)-4-(t-butyldimethylsilyloxy)-3-(N-methoxy-N-methyl-carboxamido)-2-(3-pyridyl)tetrahydrofurane as an oil with elemental analysis: C, 59.26; H, 8.51; N, 8.04 (theory: C, 58.99; H, 8.25; N, 7.64) and optical rotation $[\alpha]_D25 = -4.26$ (8.3 mg/ml, methanol).

To a solution of 19.22 g (0.0524 mol) of (2S,3S,4S)-4-(t-butyldimethylsilyloxy)-3-(N-methoxy-N-methylcarboxamido)-2-(3-pyridyl)tetrahydrofurane in 875 ml of anhydrous ether 2.51 g (0.066 mol) of lithium aluminum hydride is added in portions, with stirring at $-5°$ C., over a period of 5 min. The mixture is stirred at $-5°$ C. for ½ h and a solution of 18.25 g (0.134 mol) of potassium bisulfate in 43 mL of water is added dropwise. The mixture is diluted with ether and washed with water and brine, dried (MgSO4) and evaporated to give 18.95 g of (2S,3S,4S)-4-(t-butyldimethylsilyloxy)-2-(3-pyridyl)tetrahydrofuran-3-carboxaldehyde as an oil.

To a solution of 9.75 g (0.0292 mol) of (2S,3S,4S)-4-(t-butyldimethylsilyloxy)2-(3-pyridyl)tetrahydrofuran-3-carboxaldehyde in 120 ml of methylene chloride is added 9.75 g (0.0292 mol) of methyl (triphenylphosphoranylidene)acetate, the mixture is stirred at room temperature overnight and evaporated. The residue is triturated with ether to precipitate out most of the triphenylphosphine oxide, filtered and washed with ether. The filtrates are evaporated and the residue is purified by flash chromatography from silica gel (5×9 cm²) using methylene chloride-ethyl acetate (1:1) as eluent to give 6.77 g of methyl (E)-(2S,3S,4S)-3-[4-(t-butyl-dimethylsilyloxy)-2-(3-pyridyl)tetrahydrofuran-3-yl]-2-propenoate with elemental analysis: C, 62.67; H, 8.12; N, 3.86 (theory: C, 62.78, H, 8.04; N, 3.85) and optical rotation $[\alpha]_D25 = +26.77$ (8.9 mg/ml methanol).

A solution of 6.7 g (0.0184 mol) of methyl (E)-(2S,3S,4S)-3-[4-(t-butyldimethylsilyloxy)-2-(3-pyridyl)-tetrahydrofuran-3-yl]-2-propenoate in 94 mL of ethanol is hydrogenated over 0.7 g of 10% palladium on carbon catalyst at atmospheric pressure. The catalyst is filtered, washed with ethanol and the filtrates are evaporated to dryness to give methyl (2S,3S,4S)-3-[4-(t-butyl-dimethylsilyloxy)-2-(3-pyridyl)tetrahydrofuran-3-yl]propanoate as an oil with elemental analysis: C, 62.77; H, 8.35: N, 3.84 (theory: C, 62.43: H, 8.55: N, 3.83).

Alternatively the later compound is prepared as follows:

A solution of 1.93 g (0.0053 mol) of methyl (E)-(2S,3S,4S)-3-[4-(t-butyldimethyl-silyloxy)-2-(3-pyridyl)tetrahydrofuran-3-yl]-2-propenoate and 67 mg (0.28 mmol) of nickel dichloride hexahydrate in 17 ml of methanol is cooled to 0° C. and 0.21 g (0.0054 mol) of sodium borohydride is added in portions over a period of 20 min. The mixture is stirred at 0° C. for another 15 min and at room temperature for 1 h, evaporated to dryness, the residue is triturated with water and ethyl acetate and filtered through a celite bed. The aqueous layer of the filtrate is separated and extracted with ethyl acetate. The combined ethyl acetate extracts are washed with brine, dried (MgSO4) and evaporated to give methyl (2S,3S,4S)-3-[4-(-t-butyldimethylsilyloxy)-2-(3-pyridyl)tetrahydrofurane-3-yl]propanoate as an oil. Flash chromatography of the crude product gave 0.8 g of analytically pure material.

To a solution of 1.82 g of methyl (2S,3S,4S)-3-[4-(t-butyldimethylsilyloxy)-2-(3-pyridyl)-tetrahydrofuran-3-yl]propanoate in 25 ml of methanol is added 10 ml (0.01 mol) of 1N sodium hydroxide, the mixture is stirred at room temperature overnight, evaporated to a small volume and extracted with ethyl acetate. The aqueous layer is diluted with 20 ml of methylene chloride, the mixture is cooled to 0° C. and the pH of the aqueous layer is adjusted with stirring to 5.5 with 2N aqueous hydrochloric acid. The methylene chloride layer is dried (MgSO4) and evaporated. The residue is triturated with ethyl acetate to give (2S,3S,4S)-3-[4-(t-butyldimethylsilyloxy)-2-(3-pyridyl)tetrahydrofuran-3-yl]propanoic acid with mp 93°–94° C.

To a solution of 51.8 g (0.141 mol) of methyl (2S,3S,4S)-3-[4-(t-butyldimethylsilyloxy)-2-(3-pyridyl)-tetrahydrofuran-3-yl]propanoate in 900 ml of methylene chloride, 283 ml (0.283 mol) of 1M solution of diisopropylaluminum hydride in methylene chloride is added dropwise with stirring under agron at $-78°$ C. over a period of 50 min. The mixture is stirred at $-78°$ C. for another 50 min and 141 ml of methanol are added dropwise. The cooling bath is removed, the mixture is diluted with 3.4 l of ethyl ether, 100.5 g of dry sodium sulfate and 141 ml of brine are added and the resultant mixture is stirred at room temperature for 5 h. The solids are filtered and washed with ether and the filtrates are evaporated to dryness to give (2S,3S,4S)-3-[4-(t-butyldimethylsilyloxy)-2-(3-pyridyl)tetra-hydrofurane-3-yl]propanal as an oil, which is used in the next step without purification.

Alternatively the latter compound is prepared as follows:

To a solution of 10.86 g (0.0309 mol) of (2S,3S,4S)-3-[4-t-butyldimethylsilyloxy)-2-(3-pyridyl)tetrahydrofuran-3-yl]propanoic acid in 222 ml of methylene chloride are added with stirring 3.62 g (0.037 mol) of N,O-dimethyl hydroxylamine hydrochloride, 6.27 g (0.041 mol) of 1-hydroxybenzotriazole monohydrate, 11.86 g (0.0619 mol) of 1-(3-dimethylaminopropyl)-3-ethylcarbodiimide hydrochloride, 3.75 g (5.17 ml, 0.0371 mol) of triethylamine. The mixture is stirred at room temperature overnight and evaporated. The residue is triturated with ether and washed with water (2×), 10% aq. potassium carbonate, and brine, dried (MgSO4) and evaporated. The residue is dissolved in 516 ml of ether, the solution is cooled to $-5°$ C. and 1.48 g (0.039 mol) of lithium aluminum hydride is added in portions with stirring over a period of 5 min. The mixture is stirred at $-5°$ C. for ½ h and a solution of 10.76 g of potassium bisulfate in 25 ml of water is added dropwise. The mixture is washed with water and brine dried (MgSO4) and evaporated to give (2S,3S,4S)-3-[4-(t-butyldimethyl-silyloxy)-2-(3-pyridyl)tetrahydrofuran-3-yl]-propanal as an oil, which is used in the next step without purification.

To a suspension of 61.85 g (0.137 mol) of (3-carbomethoxy-1-propyl)triphenylphosphoniumbromide in 290 ml of tetrahydrofurane are added dropwise at 0° C. over argon with stirring, 116 ml (0.116 mol) of 1M solution of potassium tert-butoxide in tetrahydrofurane over a period of 20 min. The mixture is stirred at 0° C. for 1 h and a solution of 29.6 g of (2S,3S,4S)-3-[4-(t-butyldimethyl-silyloxy)-2-(3-pyridyl)tetrahydrofuran-3-yl]propanal in 150 ml of tetrahydrofurane is added dropwise over a period of 15 min. The mixture is stirred at room temperature for an additional one h, 50 ml of concentrated aqueous ammonium chloride is added and the mixture is diluted with 2000 ml of ether. The mixture is washed with water and brine and the organic layer is dried (MgSO4) and evaporated. The residue is triturated with ether, the mixture is allowed to stand in the refrigerator overnight and the precipitated triphenylphosphine oxide is filtered and washed with ether. The combined filtrates are evaporated to dryness and the residue is subjected to flash chromatography on silica gel (5×30 cm$^2$) using methylene chloride-ethyl acetate (1:1) as eluent to give 25.8 g of methyl (Z)-(2S,3S,4S)-7-[4-(t-butyldimethylsilyloxy)-2-(3-pyridyl)-tetrahydrofuran-3-yl]-4-heptenoate as an oil with elemental analysis: C,65.55; H,8.95; N,3.18 (theory: C,65.83; H,8.88; N,3.33) and optical rotation $[\alpha]_D 25 = +9.27$ (methanol).

A solution of 25.7 g (0.0612 mol) of methyl (Z)-(2S,3S,4S)-7-[4-(t-butyldimethylsilyloxy)-2-(3-pyridyl)-tetrahydrofuran-3-yl]-4-heptenoate in 257 ml of methanol is bubbled with HCl gas for about 2 min to give a strongly acidic solution. The mixture is allowed to stand at 0° C. overnight and evaporated. The residue is dissolved in 100 ml of water and extracted with ethyl acetate (2×). The ethyl acetate extracts are discarded. The aqueous layer is diluted with 150 ml of methylene chloride and neutralized by portionwise addition of potassium carbonate. The layers are separated and the aqueous layer is extracted with methylene chloride (3×). The combined extracts are washed with brine, dried (MgSO4) and evaporated to give 16.6 g of methyl (Z)-(2S,3S,4S)-7-[4-hydroxy-2-(3-pyridyl)-tetrahydrofuran-3-yl]-4-heptenoate as an oil with elemental analysis: C,65.87; H,7.78; N,4.58 (theory: C,66.86; H,7.59; N,4.58) and optical rotation $[\alpha]_D 25 = +9.44$ (methanol) and mass spectrum m/z 306 (M+1) (cald. MW=305.38).

To a solution of 12.97 g (0.0425 mol) of methyl (Z)-(2S,3S,4S)-7-[4-hydroxy-2-(3-pyridyl)-tetrahydrofuran-3-yl]-4-heptenoate, 26.57 g (0.101 mol) of triphenylphosphine and 3.32 g (2.72 mL, 0.069 mol) of 95% formic acid in 130 ml of tetrahydrofurane is added dropwise with stirring under argon at 10° C. 17.63 g (15.94 ml, 0.101 mol) of diethyl azodicarboxylate over a period of 10 min. The mixture is stirred at room temperature for one h and evaporated. The residue is triturated with ether and the mixture is allowed to stand at 0° C. overnight. The precipitated triphenylphosphine oxide is filtered and washed with ether. The combined filtrates and washings are evaporated to dryness. The residue is dissolved in 130 ml of methanol and hydrogen chloride gas is bubbled through the solution for 3 to 5 min. The mixture is stirred for 30 min and evaporated to dryness. The residue is dissolved in 56 ml of water and the solution is extracted with ethyl acetate (3×). The aqueous layer is mixed with 100 ml of methylene chloride and neutralized with solid sodium bicarbonate with vigorous stirring. The layers are separated and the aqueous layer is extracted with methylene chloride (3×). The combined methylene chloride extracts are washed with brine, dried (MgSO4) and evaporated to give 12.68 g of methyl (Z)-(2S,3S,4R)-7-[4-hydroxy-2-(3-pyridyl)-tetrahydrofuran-3-yl]-4-heptenoate as oil with elemental analysis: C,66.1; H,7.36; N,4.89 (theory: C,66.86; H,7.59; N,4.59) and mass spectrum m/z 306 (M+1) (Calcd. MW=305.38).

A 35% suspension of potassium hydride in mineral oil (2.07 g, 0.018 mol) is washed twice with petroleum ether under argon. The residual potassium hydride is suspended in 88.6 ml of dry tetrahydrofurane and the suspension is cooled with stirring to −10° C. To the stirred suspension a solution of 5.54 g (0.018 mol) of methyl (Z)-(2S,3S,4R)-7-[4-hydroxy-2-(3-pyridyl)tetrahydrofuran-3-yl]-4-heptenoate in 20 ml of tetrahydrofurane is added at once, the mixture is stirred at −10° C. for 2 min, and 5.4 g (0.018 mol) of 4-iodomethylbiphenyl is added at once and the mixture is stirred for 1 h. The reaction mixture is quenched with 10 ml of conc. aqueous ammonium chloride, diluted with 200 ml of ether and washed with water (2×), brine, dried (MgSO4) and evaporated. The residue is purified by flash chromatography from silica gel (5×30 cm$^2$) using ethyl acetate-methylene chloride (1:1) as eluant to give 5.8 g of methyl (Z)-(2S,3S,4R)-7-[4-(1,1'-biphenyl-4-ylmethoxy)-2-(3-pyridyl)tetrahydrofuran-3yl[-4-heptenoate as oil with elemental analysis: C,76.16; H,6.89; N,2.88 (theory: C,76.406; H,7.05; N,2.97) and optical rotation $[\alpha]_D 25 = +95.70$ (11.3 mg/ml, methanol).

EXAMPLE 3

An alternative method of preparation of the synthetic intermediate (2α,3β)-3-(3-t-butyldiphenylsilyloxyprop-1-yl)-2-(3-pyridyl)tetrahydrofuran-4-one described in Example 1 is as follows:

To a solution of lithium diisopropylamide prepared by adding at 0° C. 6.1 ml (0.0122 mole) of 2.01 molar solution of n-butyllithium to a stirring solution of 1.23 g (0.0122 mole) of diisopropyl amine in 25 ml of ether and cooling the solution to −78° C., a solution of 1.2 g (0.0122 mole) of δ-valerolactone in 2 ml of ether is added dropwise over a period of 5 min. The mixture is stirred at −78° C. for 1 h and a solution of 2.12 g (0.0122 mole) of t-butyldimethylsilyloxyacetaldehyde in 2 ml of ether is added dropwise and the mixture is stirred at −78° C. for 40 min. The resulting solution, is transferred via a glass cannula into a stirred suspension of 3-lithiopyridine prepared by adding dropwise 1.56 g (0.0162 mole) of 3-bromopyridine into a solution of 7.4 ml (0.0149mole) of 2.01 molar solution of n-butyllithium in hexane in 60 ml of ether at −78° C. and stirring the mixture for ½ h. The mixture is stirred at −78° C. for 1 h and quenched with 20 ml of concentrated aqueous ammonium chloride. The mixture is warmed to 10° C. washed with 10 ml of water and brine, dried (MgSO4) and evaporated. The residue is purified by flash chromatography using methylene chloride-methanol-ammonium hydroxide (300:25:1) as eluent to give 1-(t-butyldimethylsilyloxy)-3-nicotinoylhexan-2,6-diol as an oil.

To a solution of 4.69 g (0.0133 mole) of 1-(t-butyldimethylsilyloxy)-3-nicotinoylhexan-2,6-diol, 2.18 g (0.032 mole) of imidazole in 12 ml of dimethylformamide is added at once 4.38 g (0.0159 mole) of t-butyldiphenylchlorosilane, the mixture is stirred at room temperature overnight, diluted with 30 ml of ethyl acetate and washed with water (2×10 ml) and brine, dried (MgSO4) and evaporated. The residue is purified by flash chromatography using ethyl acetate-methylene chloride (2:3) as eluent to give 1-(t-butyldimethylsilyloxy)-6-(t-butyldiphenylsilyloxy)-3-nicotinoylhexan-2-ol as an oil.

To a solution of 4.83 g (0.00818 mole) of 1-(t-butyldimethylsilyloxy)-6-(t-butyldiphenylsilyloxy)-3-nicotinoylhexan-2-ol in 25 ml of ethanol-acetic acid (9:1) is added in portions 1.23 g (0.0325 mole) of sodium borohydride with stirring at 0° C. over a period of 15 min. After stirring at 0° C. for 1 h the mixture is evaporated. The residue is triturated with ethyl acetate and neutralized with concentrated aqueous sodium bicarbonate. The aqueous layer is extracted two more times with ethyl acetate and the combined organic extracts are washed with water and brine, dried (MgSO$_4$) and evaporated to give 1-(t-butyldimethylsilyloxy)-6-(t-butyldiphenylsilyloxy)-3-[α-hydroxy-(3-pyridyl)methyl]hexan-2-ol as an oil.

A solution of 1.2 g (0.00201 mole) 1-(t-butyldimethylsilyloxy)-6-(t-butyl-diphenyl-silyloxy)-3-[α-hydroxy-(3-pyridyl)methyl]hexan-2-ol in 12 ml of acetic acid-water (4:1) is stirred at room temperature for 15 h and evaporated. The residue is triturated with ethyl acetate and neutralized with concentrated aqueous sodium bicarbonate. The aqueous layer is extracted two more times with ethyl acetate and the combined ethyl acetate extracts are dried (MgSO$_4$) and evaporated. The residue is purified with flash chromatography using methylene chloride-methanol-ammonium hydroxide (300:25:10) as eluent to give 6-(t-butyldiphenyl-silyloxy)-3-[α-hydroxy-(3-pyridyl)methyl]hexan-1,2-diol as an oil.

To a solution of 2.91 g (0.00607 mole) of 6-(t-butyldiphenylsilyloxy)-3-[α-hydroxy-(3-pyridyl)methyl]hexan-1,2-diol and 4.89 g (0.0618 mole) of pyridine in 60 ml of methylene chloride is added at once 1.29 g (0.00667 mole) of p-toluenesulfonyl chloride at 0° C. with stirring. The mixture is allowed to warm up slowly to room temperature and stirred for 15 h. An additional 0.6 g (0.0031 mole) of p-toluenesulfonyl chloride is added and the mixture is stirred for another 5 h and evaporated. The residue is taken up in ethyl acetate and washed with water and brine, dried (MgSO$_4$) and evaporated. The residue is purified by flash chromatography using methylene chloride-methanol-ammonium hydroxide (300:25:1) as eluent to give 3-(3-t-butyldiphenylsilyloxyprop-1-yl)-4-hydroxy-2-(3-pyridyl)tetrahydrofuran as an oil.

This compound was convened to (2α,3β)-2-(3-t-butyldiphenylsilyloxyprop-1-yl)-2-(3-pyridyl)tetrahydrofuran-4-one in a similar manner described for the preparation of (2α,3β)-2-(3-t-butyldimethylsilyloxyprop-1-yl)-2-(3-pyridyl)tetrahydrofuran-4-one in example 1.

EXAMPLE 4

An alternative method of preparation of the synthetic intermediate 6-(t-butyldiphenylsilyloxy)-3-[α-hydroxy-(3-pyridyl)methyl]hexan-1,2-diol described in Example 3 is as follows:

To a solution of 18.18 g (0.18 mole) of diisopropylamine in 360 ml of tetrahydrofuran is added dropwise at 0° C. with stirring under argon 85.14 ml (0.18 mole) of 2.01 molar solution of n-butyllithium in hexane. The mixture is stirred at 0° C. for 5 min, cooled to −78° C. and a solution of 18 g (0.18 mole) of δ-valerolactone in 60 ml of tetrahydrofuran is added dropwise over a period of 30 min. The mixture is stirred at −78° C. for an additional 45 min and a solution of 19.2 g (0.18 mole) of pyridine-3-carboxaldehyde in 30 ml of tetrahydrofuran is added dropwise over a period of 10 min. The mixture is stirred at −78° C. for an additional 10 min, 36 ml (0.304 mole) of chlorotrimethylsilane are added at once and the mixture is allowed to warm up slowly to room temperature overnight. The mixture is diluted with 500 ml of ether and washed with concentrated aqueous sodium bicarbonate (3×50 ml), brine, then dried (MgSO$_4$) and evaporated. The residue is purified by flash chromatography using methylene chloride-ethyl acetate-methanol (40:9:1) to give (2H)-3-[(3-pyridyl)-α-trimethylsilyloxymethyl]-3,4,5,6-tetrahydropyran-2-one as a crystalline material, mp 50°–55° C.

To a suspension of 4.4 g (0.039 mole) of freshly sublimed potassium tert-butoxide in 224 ml of dry tert-butylmethyl ether is added dropwise at −78° C. with stirring under argon, 29.8 ml (0.039 mole) of 1.3 molar solution of sec-butyllithium in hexane and the mixture is stirred for additional 2 h. A 2 molar solution of lithium bromide (39.2 ml) in tetrahydrofuran is added dropwise. The mixture is allowed to warm up to −10° C. over a period of 30 min and then cooled to −78° C. A solution of 8.1 g (0.029 mole) of (2H)-3-[(3-pyridyl)-α-trimethylsilyloxymethyl-3,4,5,6-tetrahydropyran-2-one in 20 ml of tetrahydrofuran is added dropwise, the mixture is stirred for 45 min, allowed to warm up to −30° C., quenched with 30 ml of concentrated aqueous ammonium chloride, washed with water and brine, dried (MgSO$_4$) and evaporated to give 1-(t-butyloxy)-6-hydroxy-3-[(3-pyridyl)-α-trimethylsilyloxymethyl]hexan-2-one as an oil.

A solution of 10.6 g (0.029 mole) of 1-(t-butyloxy)-6-hydroxy-3-[(3-pyridyl)-α-trimethylsilyloxymethyl]hexan-2-one, 8.4 g (0.0306 mole)of t-butyldiphenylchlorosilane, 4.5 g (0.067 mole) of imidazole in 30 ml of dimethylformamide is stirred at room temperature for 15 h, diluted with 200 ml of ether and washed with water (2×100 ml) and brine, dried (MgSO$_4$) and evaporated. The residue is purified by flash chromatography using methylene chloride-ethyl acetate 4:1 as eluent to give 1-(t-butyloxy)-6-(t-butyl-diphenylsilyloxy)-3-[(3-pyridyl)-α-trimethylsilyloxymethyl]hexan-2-one as an oil.

To a solution of 1.6 g (0.0026 mole) of 1-(t-butyloxy)-6-(t-butyldiphenylsilyloxy)-3-[(3-pyridyl)-α-trimethylsilyloxymethyl]hexan-2-one in 10 ml of ethanol to added in portions 252 mg (0.007 mole) of sodium borohydride over a period of 10 min, the mixture is stirred at room temperature for 2 h and evaporated. The residue is triturated with ethyl acetate, washed with water and brine, dried (MgSO$_4$) and evaporated to give 1-(t-butyloxy)-6-(t-butyldiphenylsilyloxy)-3-[α-hydroxy-(3-pyridyl)methyl]hexan-2-ol as an oil.

A solution of 175 mg of 1-(t-butyloxy)-6-(t-butyldiphenylsilyloxy)-3-[α-hydroxy-(3pyridyl)methyl]hexan-2-ol in 1 ml of trifluoroacetic acid is stirred at room temperature for 30 min, diluted with toluene and evaporated. The residue is triturated with ethyl acetate, neutralized with concentrated aqueous sodium bicarbonate, dried (MgSO$_4$) and evaporated to give 6-(t-butyldiphenylsilyloxy)-3-[(α-hydroxy-(3-pyridyl)methyl]hexan-1,2-diol described in example 2.

EXAMPLE 5

An alternative method of preparation of the synthetic intermediate 6-(t-butyldiphenylsilyloxy)-3-(α-hydroxy-3-pyridylmethyl)hexan-1,2-diol described in Example 3 is as follows:

To a solution of 14 g (0.05 mol) of (2H)-3-(3-pyridyl-α-trimethylsilyloxymethyl)-3,4,5,6-tetrahydropyran-2-one described in Example 4, in 250 ml of methylene chloride is added dropwise with stirring under argon at −78° C., 60.1 ml (0.06 mol) of 1 molar solution of diisobutyl aluminum hydride in methylene chloride over a period of ½ h. The mixture is stirred for an additional 45 min, quenched with 30 ml of methanol and diluted with 500 ml of ether. To the resulted solution are added 30 ml of brine and 21.7 g of sodium sulfate and the stirring continues at room temperature overnight. The solids are filtered and washed with ether and the filtrates are evaporated to dryness. The residual oil is dissolved in 240 ml of methylene chloride and the solution is added with stirring to a solution of 12.5 g (0.25 mol) of sodium cyanide in 223 ml of water. To the resulted mixture 342 ml of 1N hydrochloric acid is added and stirring is continued at room temperature overnight. The methylene chloride layer is separated and discarded. To the aqueous layer 12.55 g of sodium cyanide and 256 ml of 1N hydrochloric acid are added and the mixture is stirred for 5 h, hydrogen chloride gas is bubbled into the solution for 10 min and the mixture is stirred at 80° C. overnight. The mixture is evaporated to dryness, the residue is dissolved in 150 ml of water and the solution is neutralized with solid sodium bicarbonate. The mixture is extracted once with ethyl acetate and the extracts are discarded. The aqueous layer is evaporated to dryness, the residue is triturated with ethanol and the solids are filtered and washed with ethanol. The ethanolic filtrates are evaporated to dryness and the residue is dried under high vacuum to give 19.35 g of crude 2-hydroxy-3-(3-hydroxy-1-propyl)-4-(3-pyridyl)-γ-butyrolactone as a thick oil.

To a solution of 37.23 g (0.157 mol) of the crude 2-hydroxy-3-(3-hydroxy-1-propyl)-4-(3-pyridyl)-γ-butyrolactone in 170 ml of dimethylformide are added 21.4 g (0.157 mol) of imidazole and 23.63 g (0.157 mol) of t-butyldiphenylchlorosilane and the mixture is stirred at room temperature overnight. The mixture is diluted with ethyl acetate and washed with water (2×), brine, dried (MgSO4) and evaporated. The residue is purified by flash chromatography from silica gel using ethyl acetate:methylene chloride (1:1) as eluent to give 3-[3-(t-butyldiphenylsilyloxy)-1-propyl]-2-hydroxy-4-(3-pyridyl)-γ-butylactone which crystallizes from ether-petroleum ether and having mp 81°–84° C. and elemental analysis: C, 61,52; H, 8.21; N, 3.91 (theory, C, 61.50; H, 8.32; N, 3.98).

To a solution of 5 g (0.014 mol) of 3-[3-(t-butyldiphenylsilyloxy)-1-propyl]-2-hydroxy-4-(3-pyridyl)-γ-butylactone in 50 mL of dry tetrahydrofurane are added in portions with stirring 0.7 g (0.018 mol) of lithium aluminum hydride and the mixture is refluxed for 10 h. The mixture is quenched with 0.7 ml of water and 0.7 ml of 15% aq. sodium hydroxide, diluted with ether and stirred for 1.5 h. The solids are filtered and washed with ether and the filtrates are evaporated to dryness. The residue is purified by flash chromatography from silica gel using methylene chloride-methanol-concentrated ammonium hydroxide as eluent to give 6-(t-butyldiphenylsilyloxy)-3-(α-hydroxy-3-pyridylmethyl)-hexan-1,2-diol described in Example 3.

EXAMPLE 6

An alternative method for the preparation of the intermediate 1-(t-butyldimethylsilyloxy)-6-(t-butyldiphenylsilyloxy)-3-nicotinoylhexan-2-ol described in Example 3 is as follows:

To a solution prepared by adding 497 ml (1 mole) of 2.01 molar solution of n-butyllithium in hexane into 2 l of ether at −60° C., is added dropwise with stirring under argon at −78° C. a solution of 172 g (1.09 mole) of 3-bromopyridine in 50 ml of ether over a period of 15 min. The mixture is stirred at −78° C. for an additional 30 min and a solution of 100 g(1 mole) of δ-valerolactone in 100 ml of ether is added dropwise over a period of 15 min. The mixture is stirred at −78° C. for 3 h, quenched with 500 ml of concentrated aqueous ammonium chloride, washed with water, dried (MgSO4) and evaporated to give 5-hydroxy-1-(3-pyridyl)pentan-1-one as an oil.

A solution of 4.59 g (0.0256 mole) of 5-hydroxy-1-(3-pyridyl)pentan-1-one, 3.82 g (0.0561 mole) of imidazole 7.76 g (0.0282 mole) of tert-butyldiphenylsilylchloride in 10 ml of dimethylformamide is stirred at room temperature for 15 h, diluted with 75 ml of water and extracted with ethyl acetate (2×50 ml). The extracts are washed with water and brine, dried (MgSO4) and evaporated. The residue is purified by flash chromatography using methylene chloride-ethyl acetate (4:1) as eluent to give 5-(t-butyldiphenylsilyloxy)-1-(3-pyridyl)pentan-1-one as an oil.

To a solution of 0.93 ml (0.0044 mole) of hexamethyldisilazane in 14 ml of tetrahydrofuran, 2.15 ml (0.0044 mole) of 2.06 molar solution of n-butyllithium in hexane is added dropwise with stirring under argon at 0° C. The mixture is cooled to −20° C. and a solution of 1.68 g (0.004 mole) of 5-(t-butyldiphenylsilyloxy)-1-(3-pyridyl)pentan-1-one in 10 ml of tetrahydrofuran is added dropwise over a period of 15 min. The mixture is stirred at −20° C. for 15 min and a solution of 0.74 g (0.0042 mole) of t-butyldimethylsilyloxy acetaldehyde in 15 ml of tetrahydrofurane is added over a period of 1 min. The mixture is stirred at −20° C. for 15 min, quenched with 6 ml of concentrated aqueous ammonium chloride, diluted with ether and washed with water and brine, dried and evaporated. The residue is purified by flash chromatography using ethyl acetate-methylene chloride (1:1) as eluent to give 1-(t-butyldimethylsilyloxy)-6-(t-butyldiphenylsilyloxy)-3-nicotinoylhexan-2-ol described in example 3.

EXAMPLE 7

(Z)-(2R,3R,4S)-7-[4-(biphenyl-4-ylmethoxy)-2-(3-pyridyl)tetrahydrofuran-3-yl]hept-4-enoic acid having mp 94°–96° C. and $[\alpha]_D^{25} = -83.75°$ (MeOH) is prepared from (2R,3R,4S)-3-(3-t-butyldimethylsilyloxypropan-1-yl)-4-[(R)-(−)-α-methoxyphenylacetoxy]-2-(3-pyridyl)tetrahydrofuran as described for the synthesis of (Z)-(2S,3S,4R)-7-[4-(biphenyl-4-ylmethoxy)-2-(3-pyridyl)tetrahydrofuran-3-yl]hept-4-enoic acid in example 1.

EXAMPLE 8

(a) The isomer (2α,3β,4β)-3-(3-t-butyldimethylsilyloxypropyl)-4-hydroxy-2-(3-pyridyl)-tetrahydrofuran is converted to the racemic (Z)-(2α,3β,4β)-7-[4-(biphenyl-4-yl-methoxy)-2-(3-pyridyl)tetrahydrofuran-3-yl)hept-4-enoic acid, mp 108°–110° C., as described in example 1 for the preparation of its (+) and (−) enantiomers.

(b) In a similar manner the corresponding (2α,3α,4α)-3-(3-t-butyldimethyl-silyloxypropyl)-4-hydroxy-2-(3-pyridyl)tetrahydrofuran is converted to the racemic (Z)-(2α,3α,4α)-7-[4-(biphenyl-4-ylmethoxy)-2-(3-pyridyl)tetrahydrofuran-3-yl]-hept-4-enoic acid obtained as an oil.

The starting materials are prepared as follows:

A solution of 15.2 g (0.0607 mole) of 2-(3-benzyloxypropyl)-3-hydroxy-γ-butyrolactone, 11.69 g (0.09 mole) of diisopropylethylamine, 11.45 g (0.0907 mole) of 2-methoxyethoxymethyl chloride in 56 ml of methylene chloride, is heated at 45° C. for 15 h and evaporated. The residue is triturated with 100 ml of ether, washed with water (3×30 ml) and brine, dried (MgSO₄) and evaporated to give a mixture of two isomers. Flash chromatography of the mixture using methylene chloride-ethyl acetate 4:1 as eluent gives the less polar (2β,3α)-2-(3-benzyloxypropyl)-3-(2-methoxyethoxymethoxy)-γ-butyrolactone and the polar (2α,3α)-2-(3-benzyloxypropyl)-3-(2-methoxyethoxy-methoxy)-γ-butyrolactone isomers as oils.

A mixture of 6.25 g (0.0184 mole) of (2α,3α)-2-(3-benzyloxypropyl-3-(2-methoxyethoxymethoxy)-γ-butyrolactone and 200 mg of 10% palladium on carbon in 50 ml of ethanol and 7 ml of acetic acid is hydrogenareal at 45 psi at room temperature for 15 h, filtered and evaporated to give (2α,3α)-2-(3-hydroxypropyl)-3-(2-methoxy-ethoxymethoxy)-γ-butyrolactone as an oil.

A solution of 10.1 g (0.0406 mole) of (2α,3α)-2-(3-hydroxypropyl)-3-(2-methoxyethoxymethoxy)-γ-butyrolactone, 7.77 g (0.051 mole) of t-butyldimethylchlorosilane and 6.93 g (0.1 mole) of imidazole in 61 ml of dimethylformamide is stirred at room temperature for 15 h. The mixture is diluted with ethyl acetate, washed with water (2×30 ml) and brine, dried (MgSO₄) and evaporated. The residue is purified with flash chromatography using methylene chloride-ethyl acetate (4:1) to give (2α,3α)-2-(3-t-butyldimethylsilyloxypropyl)-3-(2-methoxyethoxymethoxy)-γ-butyrolactone as an oil.

A solution of 5.2 g (0.033 mole) of 3-bromopyridine in 50 ml of ether is added dropwise with stirring under argon at −78° C., to a solution of 14.8 ml (0.03 mole) of 2.01 molar solution of n-butyllithium in hexane in 150 ml of ether over a period of 20 min. The mixture is stirred for another ½ h and a solution of 10.9 g (0.03 mole ) of (2α,3α)-2-(3-t-butyldimethylsilyloxypropyl)-3-(2-methoxyethoxymethoxy)-γ-butyrolactone is added dropwise over a period of 10 min. The mixture is stirred at −78° C. for 2 h, allowed to warm up to −20° C. and quenched with 7 ml of concentrated aqueous ammonium chloride. The mixture is washed with water and brine, dried (MgSO₄) and evaporated. The residue is purified by flash chromatography using methylene chloride-ethyl acetate-methanol (20:4:1) as eluent to give (2,3-erythro)-6-(t-butyldimethysilyloxy)-2-(2-methoxyethoxymethoxy)-3-nicotinoylhexan-1-ol as an oil.

To a solution of 8.54 g (0.0193 mole) of (2,3-erythro)-6-(t-butyldimethysilyloxy)-2-(2-methoxyethoxymethoxy)-3-nicotinoylhexan-1-ol in 45 ml of ethanol, is added in portions 734 mg (0.0194 mole) of sodium borohydride, the mixture is stirred at room temperature for 15 h and evaporated. The residue is triturated with ethyl acetate-ether (1:1), washed with water and brine, dried (MgSO₄) and evaporated. The residue is purified by flash chromatography using methylene chloride-methanol-ammonium hydroxide (300:25:1) as eluent to give (2,3-erythro)-6-(t-butyldimethylsilyloxy)-2-(2-methoxyethoxymethoxy)-3-[α-hydroxy-(3-pyridyl) methyl]hexan-1-ol as an oil.

To a solution of 6 g (0.0135 mole) of (2,3-erythro)-6-(t-butyldimethylsilyloxy)-2-(2-methoxyethoxymethoxy)-3-[α-hydroxy-(3-pyridyl)methyl]hexan-1-ol and 3.86 g (0.0147 mole) of triphenylphosphine in 28 ml of methylene chloride is added dropwise with stirring at 0° C., 3.28 g (0.035 mole) of diethyl azodicarboxylate over a period of 20 min. The mixture is further stirred at 0° C. for 30 min and evaporated. The residue is triturated with ether and the solution is kept at 0° C. for 1 h. The triphenylphosphine oxide is filtered and the filtrates are evaporated. The residue is taken up in 75 ml of methanol, the solution is treated with HCl gas until it becomes strongly acidic, stirred at room temperature for 1 h and evaporated. The residue is triturated with 30 ml of water and extracted with ethyl acetate (3×15 ml). The aqueous layer is evaporated to dryness and the residue is dried under high vacuum. The residue is dissolved in 38 ml of dimethylformamide, 2.76 g (0.0175 mole) of t-butyldimethylsilyl chloride and 2.47 g (0.035 mole) of imidazole are added and the solution is stirred at room temperature for 15 h and evaporated. The residue is triturated with ethyl acetate and washed with concentrated aqueous sodium bicarbonate and brine, dried (MgSO₄) and evaporated. The residue is purified by flash chromatography using methylene chloride-methanol-ammonium hydroxide (300:25:1) as eluent. The fractions containing a mixture of the two isomeric components are pooled and evaporated. The residue is dissolved in ether-pentane and the solution is cooled to 0° C. for 1 h to give after filtration crystalline (2α,3α,-4α)-3-(3-t-butyldimethylsilyloxypropyl)-4-hydroxy-2-(3-pyridyl)tetrahydrofuran, mp 99°–100° C. The mother liquids are evaporated to dryness giving the corresponding (2α,3β,4β) isomer described in the example 1.

EXAMPLE 9

The isomer (2β,3α)-2-(3-benzyloxypropyl)-3-(2-methoxyethoxymethoxy)-γ-butyrolactone described in example 8 is converted to the corresponding racemic stereoisomers (Z)-(2α,3β,4α)-7-[4-(biphenyl-4-ylmethoxy)-2-(3-pyridyl)tetrahydrofuran-3-yl]hept-4-enoic acid as oil and (Z)-(2β,3β,4α)-7-[4-biphenyl-4-ylmethoxy)-2-(3-pyridyl)tetrahydrofuran-3-yl]-hept-4-enoic acid, mp 111°–113° C., by following synthetic methodologies described in examples 8 and 1.

What is claimed is:

1. A compound of the formula

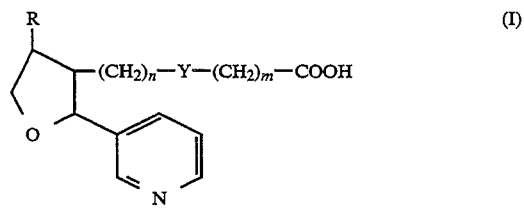

wherein R is OR' and R' is aryl-lower alkyl, biaryl-lower alkyl, lower alkyl or cycloalkyl-lower alkyl; or R is arylsulfonylamido;

wherein in the above definitions aryl represents 1- or 2-naphthyl or phenyl, or said 1- or 2-naphthyl or phenyl substituted by one or more substituents selected from halogen, trifluoromethyl, hydroxy, lower alkyl-(thio, sulfinyl or sulfonyl), lower alkoxy, lower alkyl, amino and cyano; and biaryl represents biphenyl or biphenyl substituted by one or more substituents selected from halogen, trifluoromethyl, hydroxy, lower alkyl-(thio, sulfinyl or sulfonyl), lower alkoxy, lower alkyl, amino and cyano;

n is 1, 2 or 3;

m is 1, 2 or 3;

Y is vinylene, ethylene or methyleneoxy;

a stereoisomer or optical isomer thereof; or a pharmaceutically acceptable ester thereof; or a pharmaceutically acceptable salt thereof.

2. A compound according to claim 1 of the formula

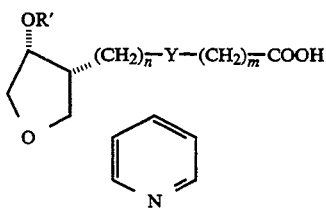

wherein R', m, n and Y have meaning as defined in claim 1; or a pharmaceutically acceptable ester thereof; or a pharmaceutically acceptable salt thereof.

3. A compound according to claim 1 of the formula

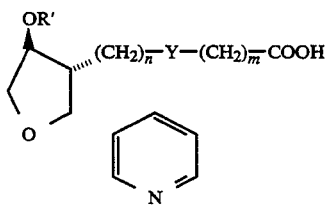

wherein R', m, n and Y have meaning as defined in claim 1; or a pharmaceutically acceptable ester thereof; or a pharmaceutically acceptable salt thereof.

4. A compound according to claim 1 wherein R is aryl-lower alkoxy or biaryl-lower alkoxy; m represents 1, 2 or 3, and n represents 1, 2 or 3 provided that the sum of m+n is 4; Y is vinylene, ethylene or methyleneoxy; or a pharmaceutically acceptable ester thereof; or a pharmaceutically acceptable salt thereof.

5. A compound according to claim 1 wherein R' is arylmethoxy or biarylmethoxy; n represents 2; m represents 2; Y is vinylene or ethylene; or a pharmaceutically acceptable ester thereof; or a pharmaceutically acceptable salt thereof.

6. A compound according to claim 1 wherein Y is vinylene.

7. A compound according to claim 1 wherein R is biphenylmethoxy; n represents 2; m represents 2; Y is vinylene; or a pharmaceutically acceptable ester thereof; or a pharmaceutically acceptable salt thereof.

8. A compound according to claim 2 wherein R' is aryl-lower alkyl or biaryl-lower alkyl; Y is ethylene or vinylene; n is 2; m is 1, 2 or 3; or a pharmaceutically acceptable ester thereof; or a pharmaceutically acceptable salt thereof.

9. A compound according to claim 8 wherein R' is biaryl-lower alkyl and Y is vinylene.

10. A compound according to claim 8 of the formula

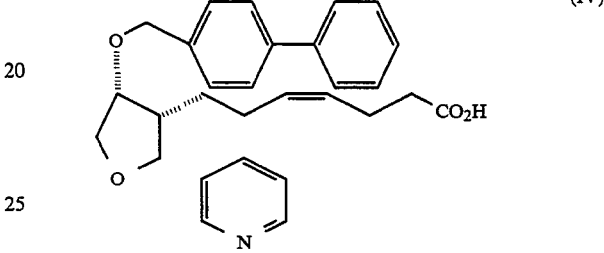

or the dextrorotatory enantiomer thereof; or a pharmaceutically acceptable ester thereof; or a pharmaceutically acceptable salt thereof.

11. A compound of formula IV according to claim 10 which is the dextrorotatory enantiomer thereof, or a pharmaceutically acceptable salt thereof.

12. A pharmaceutical composition suitable for administration to mammals for suppression of thromboxane activity comprising an effective thromboxane activity suppressing amount of a compound according to claim 1 in combination with one or more pharmaceutically acceptable carries.

* * * * *